United States Patent [19]

Leikhim et al.

[11] 4,013,574

[45] Mar. 22, 1977

[54] ORGANOSILANE-CONTAINING PRILL

[75] Inventors: John W. Leikhim, Cincinnati; Edward J. Maguire, Jr., Forest Park; David C. Heckert, Oxford; David M. Watt, Jr., Cincinnati, all of Ohio

[73] Assignee: The Procter & Gamble Company, Cincinnati, Ohio

[22] Filed: Apr. 22, 1975

[21] Appl. No.: 571,709

[52] U.S. Cl. .............................. 252/89 R; 252/99; 252/142; 260/448.2 N; 260/448.8 R; 427/212; 427/219; 427/220; 427/221

[51] Int. Cl.$^2$ .......................................... C11D 1/00

[58] Field of Search .............. 252/89, 99, 142; 427/212, 219, 220, 221; 260/448.2 N, 448.8 R

[56] References Cited

UNITED STATES PATENTS 3,624,120  11/1971  Yetter .................... 260/448.2 N

*Primary Examiner*—Mayer Weinblatt
*Attorney, Agent, or Firm*—C. R. Wilson; R. B. Aylor; T. H. O'Flaherty

[57] ABSTRACT

A prill comprising an organosilane and a water-soluble or water-dispersible, normally solid, nonionic material. The organosilane is stabilized within the prill and can be included in moisture-containing, highly alkaline or electrolyte-containing compositions, e.g. detergent compositions.

20 Claims, No Drawings

ORGANOSILANE-CONTAINING PRILL

BACKGROUND OF THE INVENTION

This invention relates to a prill containing an organosilane compound. The prills are used in detergent compositions which are intended for use on hard, i.e. metallic and vitreous surfaces. The inclusion of the hereindescribed organosilane compound in the prill assures its stability when added to compositions which contain moisture and have a high pH and/or electrolyte content.

Copending commonly assigned Patent Applications entitled "Organosilane-Containing Detergent Composition" and "Organosilane-Containing Anionic Detergent Composition" both by David C. Heckert and David M. Watt, Jr., U.S. Ser. No. 570,534, filed Apr. 22, 1975 and U.S. Ser. No. 570,533, filed Apr. 22, 1975, respectively disclose detergent compositions containing an organosilane compound. The organosilane compound is included in the detergent compositions for its soil release benefits. That is, when hard surfaces are washed with such a detergent composition, a thin polymeric layer of the organosilane compound is deposited on said surfaces. When the surfaces are thereafter soiled the soil adheres less tenaciously to the surface as a result of this polymeric coating.

Detergent compositions normally contain water and have a relativey high pH, i.e. above pH 7. Unfortunately, such conditions affect the efficacy of the organosilane compound for is intended function; that is, the organosilane compound is likely to excessively polymerize prematurely. As a result of this, the polymerized organosilane compound is not as efficient as the unpolymerized organosilane or its oligomers in properly depositing itself upon subsequently washed hard surfaces.

It has now been found that the organosilane compounds can be made more stable in a detergent composition context by forming a prill containing said organosilane and a water-soluble or water dispersible, normally solid nonionic material.

It is an object of this invention to provide a method whereby an organosilane compound can be included in a detergent composition for prolonged time intervals without the organosilane compound being significantly altered in form.

It is another object of this invention to provide a prill containing an organosilane compound and a nonionic material.

Still another object of this invention is to provide a detergent composition containing an organosilane in a form which can withstand moisture and high alkalinity and/or electrolytes.

These and other objects will become apparent from the description to follow.

As used herein, all percentages and ratios are by weight unless otherwise indicated.

SUMMARY OF THE INVENTION

A prill containing an organosilane compound which consists essentially of:
a. an organosilane having the formula

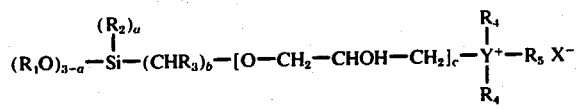

or is a siloxane oligomer thereof wherein $R_1$ is an alkyl group containing 1 to 4 carbon atoms,

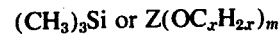

where $x$ is 2 to 4, $m$ is 1 to 20, and Z is hydrogen, an alkyl group contaning 1 to 18 carbons or an acyl group containing 1 to 4 carbon atoms; $R_2$ is an alkyl group containing 1 to 18 carbon atoms; $a$ is 0 to 2; $R_3$ is hydrogen or an alkyl group containing 1 to 18 carbon atoms; $b$ is 1 to 3; $c$ is 0 or 1; $R_4$ is an alkyl, aryl or arylalkyl group containing 1 to 12 carbon atoms, a carboxy-substituted alkyl group containing 1 to 4 carbon atoms,

where $x$, $m$ and Z are as defined above, or oxygen provided only one $R_4$ is oxygen; $R_5$ is an alkyl, aryl or arylalkyl group containing 1 to 22 carbon atoms; X is halide; and Y is nitrogen, sulfur or phosphorus; and
b. a water-soluble or water-dispersible, normally solid nonionic material in a weight ratio of organosilane to nonionic material of from 4:1 to 1:50.

DETAILED DESCRIPTION OF THE INVENTION

The prills of this invention contain an organosilane and a water-soluble or water-dispersible, normally solid, nonionic material in weight ratio of organosilane to nonionic material of from 4:1 to 1:50, preferably 2:1 to 1:5. The organosilane and nonionic materials are described in the succeeding paragraphs.

The organosilane has the formula

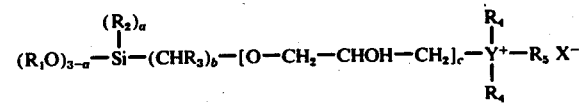

or is a siloxane oligomer thereof wherein $R_1$ is an alkyl group containing 1 to 4 carbon atoms,

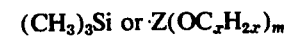

where $x$ is 2 to 4, $m$ is 1 to 20, and Z is hydrogen, an alkyl group containing 1 to 18 carbon atoms or an acyl group containing 1 to 4 carbon atoms; $R_2$ is an alkyl group containing 1 to 18 carbon atoms; $a$ is 0 to 2; $R_3$ is hydrogen or an alkyl group containing 1 to 18 carbon atoms; $b$ is 1 to 3; $c$ is 0 or 1; $R_4$ is an alkyl, aryl or arylalkyl group containing 1 to 12 carbon atoms, a carboxy-substituted alkyl group containing 1 to 4 carbon atoms,

where $x$, $m$ and Z are as defined above, or oxygen provided only one $R_4$ is oxygen; $R_5$ is an alkyl, aryl or arylalkyl group containing 1 to 22 carbon atoms; X is halide; and Y is nitrogen, sulfur or phosphorus. Preferably X is chloride or bromide and $b$ is 1.

It should be understood that the $R_4$ in the above formula and the formulae to follow may be the same or different. It should further be understood that when Y is S, there will be only one $R_4$ substituent. Also, when one $R_4$ is oxygen or, under acidic conditions, the anion of a carboxylic acid substituted alkyl, the counter ion $X^-$ is not extant. The 1 to 4 carbon atoms in the carboxy-substituted alkyl group is inclusive of the carboxyl group. The aryl or arylalkyl groups of $R_4$ and $R_5$ contain 6 to 12 carbon atoms and 6 to 22 carbon atoms, respectively.

Classes of organosilane compounds and their preparation which fit the above description follow.

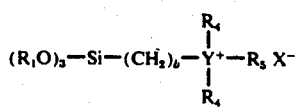     I.

wherein $R_1$ is a $C_{1-4}$ alkyl group, $b$ is from 1–3, $R_4$ is a $C_{1-12}$ alkyl, aryl or arylalkyl group, carboxy-substituted $C_{1-4}$ alkyl group,

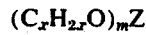

where $x$ is 2–4, $m$ is 1–20, and Z is hydrogen, a $C_{1-18}$ alkyl group or a $C_{1-4}$ acyl group, or oxygen provided only one $R_4$ is oxygen, $R_5$ is a $C_{4-22}$ alkyl, aryl or arylalkyl group, X is halide, and Y is N, S or P.

When $b$ is 3 and $R_4$ is a $C_{1-12}$ alkyl, aryl or arylalkyl group, the class of compounds represented by Formula I is prepared by the following route:

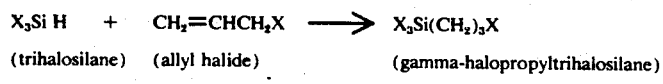

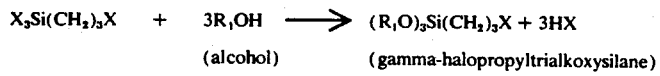

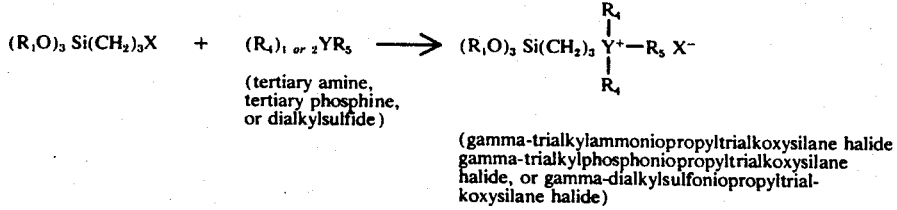

(gamma-trialkylammoniopropyltrialkoxysilane halide
gamma-trialkylphosphoniopropyltrialkoxysilane halide, or gamma-dialkylsulfoniopropyltrialkoxysilane halide)

The trihalosilane (where the halogen is chlorine or bromine) is reacted with the allyl chloride at about 100° C. for from 4 to 10 hours in the presence of a catalyst, e.g., chloroplatinic acid or platinum. The resultant -gamma-halopropyltrihalosilane is reacted with a lower alcohol to produce the gamma-halopropyltrialkoxysilane. At least three equivalents of alcohol per equivalent of halopropyltrihalosilane are added slowly to the silane. The gamma-halopropyltrihalosilane may be dissolved in an inert solvent, preferably hexane or pentane. (See W. Noll, "Chemistry and Technology of Silanes", Academic Press, New York, 1968, page 81 for the alcoholysis of halosilanes.) One equivalent of the gamma-halopropyltrialkoxysilane is reacted with one equivalent of the tertiary amine, tertiary phosphine, or dialkysulfide to produce the organosilane. An inert solvent, preferably of high dielectric constant, may be used. The reaction is carried out at temperatures of from 40° C. to 120° C. and a time of 2 to 10 hours for the reaction of the bromopropyltrialkoxysilane and 120° C. to 150° C. for 2 to 20 hours for the reaction of the chloropropyltrialkoxysilane.

The compounds of Formula I when at least one $R_4$ is a carboxy-substituted $C_{1-4}$ alkyl group are prepared in the same manner except for the last reaction step. Here, a tertiary amine, tertiary phosphine or dialkylsulfide having a carboxy-containing alkyl group(s) is reacted with the alpha, beta or gamma-haloalkyltrialkoxysilane at 50° C. to 200° C. for 2 hours to 20 hours. Such carboxy-substituted tertiary amines, tertiary phosphines, and dialkylsulfides are produced by reacting
$R_4YHR_5$ or $HYR_5$
(where Y is sulfur)
with

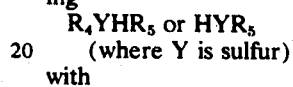

in the presence of base at elevated temperatures, e.g. 50° C. to 150° C.

The compounds of Formula I when at least one $R_4$ is

with $x$, $m$ and Z as defined above are produced in the manner given above except for the last reaction step. Thus, alpha- beta- and gamma-haloalkyltrialkoxysilane is reacted with a tertiary amine, tertiary phosphine, or dialkylsulfide where at least one substituent is

The reaction takes place at a temperature of 50° C. to 200° C. and a time of from 2 to 10 hours.

Compounds of Formula I when one $R_4$ is oxygen are prepared by following the reactions outlined above up to the last reaction step. At this point, a dialkyl amine, dialkyl phosphine or alkylthiol is reacted with the halosilane at 50° C. to 200° C. for from 4 to 10 hours and then with base to produce an intermediate tertiary amines phosphine, or dialkyl sulfide. These intermediates are then reacted with $H_2O_2$ at 20° C. to 100° C. or preferably $O_3$ in an inert solvent at $-80°$ C. to 20° C. to yield the organosilane.

When $b$ is 2 in Formula I, a trihalovinylsilane of formula $$X_3SiCH=CH_2$$

(which is commercially available) is reacted with hydrogen bromide in the presence of peroxide or light to produce a beta-haloethyltrihalosilane. This compound is reacted with an alcohol and thereafter with an appropriate amine, phosphine, or sulfide in the manner discussed above for the preparation of the compounds of Formula I when $b$ is 3.

When $b$ is 1 in Formula I, the starting reactant is a commercially available trihalomethylsilane of formula $$X_3SiCH_3.$$

This silane is reacted with chlorine or, preferably a half mole of bromine and a half mole of chlorine in the presence of light (such as provided by an ordinary tungsten or fluorescent lamp). The resultant alpha-halomethyltrihalosilane is reacted with an alcohol and thereafter an appropriate amine, phosphine or sulfide in the manner discussed above with the compounds of Formula I when $b$ is 3.

Examples of compounds illustrative of compounds of Formula I follow:
$(CH_3O)_3SiCH_2N^+(CH_3)_2C_{16}H_{33}$ $Cl^-$
$(C_2H_5O)_3SiCH_2N^+(CH_3)_2C_6H_5$ $Cl^-$
$(C_2H_5O)_3Si(CH_2)_3N^+(C_2H_5)_2C_{10}H_{21}$ $Br^-$
$(C_3H_7O)_3SiCH_2N^+(C_3H_7)_2C_6H_4CH_3$ $Br^-$
$(C_4H_9O)_3Si(CH_2)_2N^+(C_2H_5)(CH_2C_6H_5)_2$ $Cl^-$
$(CH_3O)_3SiCH_2P^+(C_2H_5)_2C_{12}H_{25}$ $Cl^-$
$(C_2H_5O)_3Si(CH_2)_3P^+(C_4H_9)_2C_6H_5$ $Cl^-$
$(C_3H_7O)_3Si(CH_2)_2S^+(CH_3)C_6H_5$ $Cl^-$
$(CH_3O)_3SiCH_2CH_2S^+(C_2H_5)$ $C_{16}H_{33}$ $Br^-$
$(CH_3O)_3SiCH_2N^+(C_2H_4COOH)_2C_{10}H_{21}$ $Br^-$
$(C_2H_5O)_3Si(CH_2)_3N^+(CH_2COOH)(CH_3)$ $C_{12}H_{25}$ $Cl^-$
$(C_2H_5O)_3Si(CH_2)_2P^+(C_3H_6COOH)(C_2H_5)C_{10}H_{21}$ $Cl^-$
$(C_4H_9O)_3SiCH_2S^+(C_3H_6COOH)C_6H_{13}$ $Br^-$
$(CH_3O)_3SiCH_2N^+(C_2H_4OH)_2C_{18}H_{37}$ $Cl^-$
$(C_4H_9O)_3Si(CH_2)_3P^+(C_3H_6OH)_2C_6H_4CH_3$ $Cl^-$
$(C_2H_5O)_3SiCH_2S^+(C_3H_6OH)C_{14}H_{29}$ $Cl^-$
$(CH_3O)_3SiCH_2N^+(O)^-(CH_3)$ $C_{14}H_{29}$
$(C_2H_5O)_3Si(CH_2)_3P^+(O)^-(C_2H_5)C_{12}H_{25}$
$(C_2H_5O)_3Si(CH_2)_2S^+(O)^-C_{10}H_{21}$
$(CH_3O)_3SiCH_2N^+[(C_2H_4O)_3H](CH_3)C_8H_{17}$ $Cl^-$
$(CH_3O)_3Si(CH_2)_2N^+[(C_4H_8O)_{15}CH_3](CH_3)C_6H_{13}$
$(C_2H_5O)_3Si(CH_2)_3N^+[(C_2H_4O)_6H]_2C_{10}H_{21}$ $Cl^-$
$(CH_3O)_3SiCH_2N^+[(C_2H_4O)_3COCH_3]_2C_8H_{17}$ $Cl^-$
$(C_3H_7O)_3SiCH_2P^+[(C_3H_6O)_{12}H]_2CH_2C_6H_5$ $Cl^-$
$(C_4H_9O)_3Si(CH_2)_3P^+[(C_2H_4O)_4C_4H_9]CH_3C_4H_9$ $Br^-$
$(CH_3O)_3Si(CH_2)_2P^+[(C_2H_4O)_5COC_2H_5]_2C_4H_9$ $Br^-$
$(CH_3O)_3SiCH_2S^+[(C_2H_4O)_5H]C_{10}H_{21}$ $Cl^-$
$(C_2H_5O)_3Si(CH_2)_2S^+[(C_3H_6O)_8C_3H_7]C_4H_9$ $Br^-$
$(CH_3O)_3Si(CH_2)_3S^+[(C_2H_4O)_{12}COC_4H_9]C_{12}H_{25}$ $Cl^-$

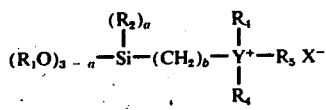

II.

where $R_1$ is a $C_{1-4}$ alkyl group, $R_2$ is a $C_{1-18}$ alkyl group $a$ is 1 or 2, $b$ is 1-3, $R_4$ is a $C_{1-12}$ alkyl, aryl or arylalkyl group, a carboxy-substituted $C_{1-4}$ alkyl group, $$(C_xH_{2x}O)_mZ$$

where $x$ is 2-4, $m$ is 1-20 and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide, and Y is N, S or P.

The compounds of Formula II are prepared in a manner similar to the preparation of the compounds of Formula I except for the fact that the starting reactants (when $b$ is 1, 2, or 3) all have a $C_{1-18}$ alkyl group or two $C_{1-18}$ alkyl groups attached to the Si atom in place of a halogen atom(s). The starting reactant is commercially available when $R_2$ is $CH_3$. When $R_2$ is $C_2H_5$ or greater, the compound is prepared by reacting a silane with an appropriate olefin. Thus, $$X_{3-a}SiH_{1+a}$$

is reacted with a $C_2$ to $C_{18}$ olefin to obtain the desired starting reactant. The remaining reaction steps and conditions for producing the desired organosilane of Formula II are essentialy the same as for producing the compounds of Formula I.

Examples of compounds of Formula II are:
$(CH_3O)_2CH_3SiCH_2N^+(CH_3)_2C_{12}H_{25}$ $Cl^-$
$(C_2H_5O)_2C_6H_{13}Si(CH_2)_2N^+(CH_3)_2C_{18}H_{37}$ $Cl^-$
$(C_3H_7O)(C_3H_7)_2Si(CH_2)_3N^+(C_2H_5)_2C_{10}H_{21}$ $Cl^-$
$(CH_3O)(CH_3)_2SiCH_2P^+(CH_3)_2C_{10}H_{21}$ $Cl^-$
$(C_3H_7O)_2C_{10}H_{21}Si(CH_2)_2S^+(C_4H_9)C_6H_{12}C_6H_5$ $Cl^-$
$(CH_3O)_2C_{16}H_{33}Si(CH_2)_3N^+(C_2H_4COOH)(CH_3)C_4H_9$ $Cl^-$
$(C_2H_5O)(CH_3)_2Si(CH_2)_2P^+(CH_2COOH)_2C_{10}H_{21}$ $Cl^-$
$(C_3H_7O)_2CH_3SiCH_2S^+(C_3H_6COOH)C_6H_{13}$ $Cl^-$
$(CH_3O)_2CH_3SiCH_2N^+(C_2H_4OH)_2C_{18}H_{37}$ $Cl^-$
$(C_3H_7O)(CH_3)_2SiCH_2P^+(C_3H_6OH)(C_4H_9)_2$ $Br^-$
$(C_4H_9O)_2CH_3Si(CH_2)_3S^+(C_3H_6OH)CH_3$ $Br^-$
$(CH_3O)_2CH_3SiCH_2N^+(O)^-(CH_3)C_{16}H_{33}$
$(CH_3O)_2C_{14}H_{29}Si(CH_2)_2P^+(O)^-(C_4H_9)_2$
$(C_4H_9O)(CH_3)_2Si(CH_2)_3S^+(O)^-C_{14}H_{29}$
$(CH_3O)_2CH_3SiCH_2N^+[(C_3H_6O)_{20}H]_2C_6H_5$ $Cl^-$
$(CH_3O)_2C_2H_5Si(CH_2)_2N^+[(C_4H_8O)_6C_2H_5]_2CH_3$ $Cl^-$
$(C_2H_5O)(CH_3)_2SiCH_2P^+[(C_2H_4O)_2H](C_6H_5)_2$ $Cl^-$
$(C_2H_5O)_2C_8H_{17}Si(CH_2)_3P^+[(C_2H_4O)_4C_6H_{13}]_2C_4H_9$ $Cl^-$
$(CH_3O)_2CH_3SiCH_2P^+[(C_2H_4O)_6COCH_3]_2C_8H_{17}$ $Cl^-$
$(CH_3O)_2CH_3SiCH_2S^+[(C_3H_6O)_2H]C_{14}H_{29}$ $Cl^-$
$(C_2H_5O)(C_2H_5)_2Si(CH_2)_3S^+[(C_2H_4O)_5CH_3[C_8H_{17}$ $Br^-$ $(C_2H_5O)_2C_{10}H_{21}SiCH_2N^+[(C_2H_4O)_2COC_2H_5](C_4H_9)_2$ $Cl^-$
$(CH_3O)_2C_4H_9Si(CH_2)_2S^+[(C_2H_4O)_2COCH_3]C_{12}H_{25}$ $Br^-$ Compounds of Formulas I and II when $R_4$ is an alkyl, aryl, arylalkyl group or oxygen are disclosed in British Patents 686,068 and 882,053 and U.S. Pat. Nos. 2,955,127, 3,557,178, 3,730,701, and 3,817,739. Compounds of Formulas I and II when $R_4$ is a carboxy-substituted alkyl group or $$(C_xH_{2x}O)_mZ$$

are disclosed in commonly assigned copending patent application "Organosilane Compounds" by Heckert and Watt U.S. Ser. No. 570,532 filed Apr. 22, 1975. (The disclosure of this application is herein incorporated by reference.)

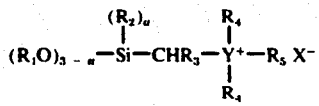

III.

wherein $R_1$ is a $C_{1-4}$ alkyl group, $a$ is 0 to 2, $R_2$ is a $C_{1-18}$ alkyl group, $R_3$ is a $C_{1-18}$ alkyl group, $R_4$ is a $C_{1-12}$ alkyl, aryl or arylalkyl group, a carboxy-substituted $C_{1-4}$ alkyl group, $$(C_xH_{2x}O)_mZ$$

where $x$ is 2–4, $m$ is 1–20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide, and Y is N, S or P.

The compounds of Formula III when $a$ is 0 and $R_4$ is an alkyl, aryl or arylalkyl group are prepared by the following route:

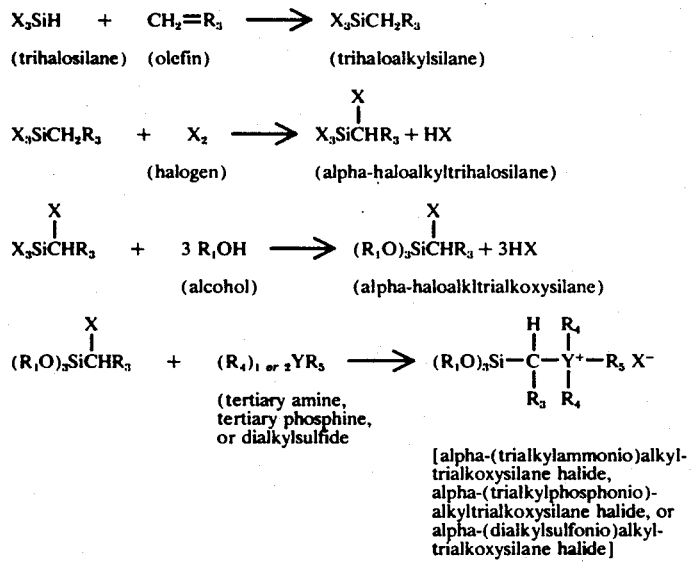

The trihalosilane is reacted with an olefin at 100° C. for 4 to 10 hours under a pressure of 50 to 300 psi. in the presence of a chloroplatinic acid or platinum catalyst to produce the trihaloalkylsilane. This reaction is reported by F. P. Mackay, O. W. Steward and P. G. Campbell in "Journal of the American Chemical Society, 79, 2764 (1957) and J. S. Speier, J. A. Webster and S. W. Barnes in Journal of the American Chemical Society, 79, 974 (1957). The trihaloalkylsilane is then halogenated in a known manner by treating it with halogen in the presence of light (such as that provided by ordinary tungsten or fluorescent lamps). Preferably, halogenation is carried out to only partial completion and a distillation is performed to recycle unreacted alkylsilane. The remaining reactions are the same as those described above in connection with the preparation of the compounds of Formula I.

When $a$ is 1 or 2, the preparation of the compounds is essentially the same except for the use of an alkyl substituted silane as the starting reactant.

When $R_4$ is a carboxy-substituted $C_{1-4}$ alkyl group, oxygen or $$(C_xH_{2x}O)_mZ$$

where $x$ is 2–4, $m$ is 1–20, and Z is hydrogen, a $C_{1-18}$ alkyl group, or a $C_{1-4}$ acyl group, an appropriate amine, phosphine, or sulfide is used in the reaction step as discussed above for the preparation of similarly substituted compounds of Formula I.

The compounds that follow are illustrative of compounds of Formula III.

$(C_2H_5O)_3SiCH(C_8H_{17})N^+(CH_3)_2C_{12}H_{25}$ Cl$^-$
$(CH_3O)_3SiCH(C_{18}H_{37})N^+(C_2H_4COOH)_2CH_3$ Cl$^-$
$(C_3H_7O)_2CH_3SiCH(C_{12}H_{25})N^+(C_2H_4OH)(CH_3)_2$ Cl$^-$
$(C_4H_9O)_3SiCH(C_3H_7)N^+[(C_2H_4O)_{10}H]_2C_6H_{13}$ Br$^-$
$(CH_3O)_3SiCH(C_{10}H_{21})N^+[(C_2H_4O)_2C_4H_9](CH_3)C_6H_5$ Br$^-$
$(CH_3O)_3SiCH(CH_3)N^+[(C_2H_4O)_3COC_2H_5](C_2H_5)_2$ Br$^-$
$(C_2H_5O)_2CH_3SiCH(C_8H_{17})N^+(O)^-(CH_3)_2$
$(CH_3O)_3SiCH(C_8H_{17})P^+(CH_3)_3$ Cl$^-$
$(CH_3O)_2CH_3SiCH(CH_3)P^+(C_3H_6COOH)_2C_{14}H_{28}C_6H_5$ Cl$^-$
$(C_2H_5O)_3SiCH(C_{10}H_{21})P^+(C_2H_4OH)C_4H_9$ Cl$^-$
$(CH_3O)_3SiCH(C_3H_7)P^+(O)^-(CH_3)C_{12}H_{25}$
$(CH_3O)_3SiCH(C_8H_{17})P^+[(C_2H_4O)_6H]_2CH_3$ Cl$^-$
$(C_2H_5O)_3SiCH(C_6H_{13})P^+[(C_3H_6O)_2C_{18}H_{37}](CH_3)_2$ Cl$^-$
$(CH_3O)_3SiCH(CH_3)S^+(CH_3)C_{16}H_{33}$ Br$^-$
$(C_2H_5O)_2CH_3SiCH(C_{12}H_{25})S^+(C_2H_4COOH)CH_3$ Cl$^-$
$(CH_3O)_2C_{16}H_{33}SiCH(C_2H_5)S^+(C_2H_4OH)C_2H_5$ Cl$^-$
$(CH_3O)_3SiCH(C_{10}H_{21})S^+(O)^-C_5H_{11}$
$(C_2H_5O)_3SiCH(C_4H_9)S^+[(C_3H_6O)_{10}H]C_6H_5$ Cl$^-$
$(C_2H_5O)_3SiCH(CH_3)S^+[(C_2H_4O)_{20}C_2H_5]CH_3$ Br$^-$

Commonly assigned copending patent application "Organosilane Compounds" by Heckert and Watt U.S. Ser. No. 570,537 filed Apr. 22, 1975 discloses the preparation of these compounds. (The disclosure of this application is herein incorporated by reference).

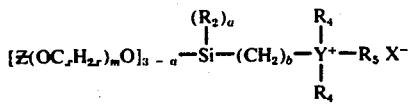

$$[Z(OC_xH_{2x})_mO]_{3-a}-\underset{\underset{R_4}{|}}{\overset{\overset{(R_2)_a}{|}}{Si}}-(CH_2)_b-\underset{\underset{R_4}{|}}{Y^+}-R_5\ X^- \quad \text{IV.}$$

wherein Z is hydrogen, a $C_{1-18}$ alkyl group or a $C_{1-4}$ acyl group, x is 2–4, m is 1–20, a is 0–2, $R_2$ is a $C_{1-18}$ alkyl group, b is 1–3, $R_4$ is a $C_{1-12}$ alkyl, aryl or arylalkyl group, a carboxy-substituted $C_{1-4}$ alkyl group, $$(C_xH_{2x}O)_mZ$$

where x, m and Z are as defined above, or oxygen provided only one $R_4$ is oxygen, $R_5$ is a $C_{1-22}$ alkyl, aryl or arylalkyl group, X is a halide, and Y is N, S or P.

The compounds with Formula IV are prepared in substantially the same manner as those of Formula II with the exception that $R_1OH$ is $$Z(OC_xH_{2x})_mOH$$

or alternatively the compounds of Formula II are heated in the presence of $$Z(OC_xH_{2x})_mOH$$

under conditions such that $R_1OH$ is removed from the system.

Exemplary compounds of Formula IV are as follows:

[CH$_3$(OC$_2$H$_4$)O]$_3$SiCH$_2$N$^+$(CH$_3$)$_2$C$_{14}$H$_{29}$ Cl$^-$
[CH$_3$(OC$_2$H$_4$)$_5$O]$_2$CH$_3$SiCH$_2$)$_3$N$^+$(CH$_2$COOH)$_2$C$_{10}$H$_{21}$ Cl$^-$
[H(OC$_3$H$_6$)$_3$O]$_3$SiCH$_2$N$^+$(C$_2$H$_4$OH)(CH$_3$)(C$_{12}$H$_{25}$) Cl$^-$
[H(OC$_2$H$_4$)$_{18}$O]$_3$Si(CH$_2$)$_2$N$^+$(O)$^-$(CH$_3$)C$_{18}$H$_{37}$
[CH$_3$CO(OC$_2$H$_4$)$_{10}$O]$_3$SiCH$_2$N$^+$[(C$_2$H$_4$O)$_{14}$H]$_2$C$_8$H$_{16}$C$_6$H$_5$ Cl$^-$
[C$_{16}$H$_{33}$(OC$_2$H$_4$)$_8$O]$_2$C$_6$H$_{13}$SiCH$_2$N$^+$[(C$_3$H$_6$O)CH$_3$]$_2$ Br$^-$
[H(OC$_4$H$_8$)$_8$O]$_3$SiCH$_2$N$^+$[(C$_2$H$_4$O)$_4$COCH$_3$]$_2$CH$_3$ Cl$^-$
[C$_6$H$_{13}$(OC$_2$H$_4$)$_2$O]$_3$Si(CH$_2$)$_2$P$^+$(CH$_3$)$_2$C$_{10}$H$_{21}$ Br$^-$
[CH$_3$(OC$_3$H$_6$)$_{14}$O]$_3$SiCH$_2$P$^+$(C$_2$H$_4$COOH)(C$_6$H$_{13}$)$_2$ Cl$^-$
[C$_2$H$_5$(OC$_2$H$_4$)O]$_2$CH$_3$Si(CH$_2$)$_2$P$^-$(C$_4$H$_8$OH)(CH$_3$)C$_6$H$_5$ Cl$^-$
[CH$_3$(OC$_2$H$_4$)$_8$O]$_3$SiCH$_2$P$^+$(O)$^-$(CH$_3$)C$_8$H$_{17}$
[C$_2$H$_5$CO(OC$_2$H$_4$)$_2$O]$_3$Si(CH$_2$)$_3$P$^+$[C$_2$H$_4$O)$_8$H]$_2$C$_6$H$_{13}$ Cl$^-$
[CH$_3$(OC$_4$H$_8$)O]$_3$SiCH$_2$P$^+$[(C$_3$H$_6$O)$_2$C$_7$H$_{15}$](C$_4$H$_9$)$_2$ Br$^-$
[C$_2$H$_5$CO(OC$_2$H$_4$)O]$_3$SiCH$_2$S$^+$(CH$_3$)C$_{18}$H$_{37}$ Cl$^-$
[H(OC$_2$H$_4$)$_4$O]$_3$Si(CH$_2$)$_2$S$^+$(C$_2$H$_4$COOH)C$_{12}$H$_{25}$ Br$^-$
[CH$_3$(OC$_2$H$_4$)$_{20}$O]$_3$Si(CH$_2$)$_3$S$^+$(C$_3$H$_6$OH)C$_{16}$H$_{33}$ Br$^-$
[H(OC$_3$H$_6$)$_{12}$O]$_3$Si(CH$_2$)$_2$S$^+$(O)$^-$C$_5$H$_{11}$
[C$_{12}$H$_{25}$(OC$_2$H$_4$)$_4$O]$_3$SiCH$_2$S$^+$[(C$_2$H$_4$O)$_{20}$H]CH$_3$ Br$^-$
[H(OC$_2$H$_4$)$_{12}$O]$_3$Si(CH$_2$)$_3$S$^+$[(C$_2$H$_4$O)C$_{14}$H$_{29}$]C$_6$H$_4$CH$_3$ Cl$^-$

Commonly assigned copending patent application "Organosilane Compounds" by Heckert and Watt U.S. Ser. No. 570,539, filed Apr. 22, 1975 discloses the preparation of these compounds. (The disclosure of this application is herein incorporated by reference.)

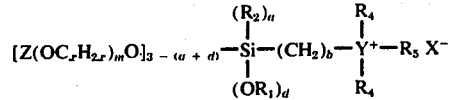

$$[Z(OC_xH_{2x})_mO]_{3-(a+d)}-\underset{\underset{(OR_1)_d}{|}}{\overset{\overset{(R_2)_a}{|}}{Si}}-(CH_2)_b-\underset{\underset{R_4}{|}}{Y^+}-R_5\ X^- \quad \text{V.}$$

wherein Z is hydrogen, a $C_{1-18}$ alkyl group or a $C_{1-4}$ acyl group, x is 2–4, m is 1–20, $R_2$ is a $C_{1-18}$ alkyl group, $R_1$ is a $C_{1-4}$ alkyl group, a is 0 or 1, d is 1 or 2 provided a+d does not exceed 2, b is 1–3, $R_4$ is a $C_{1-12}$ alkyl, aryl or arylalkyl group, a carboxy-substituted $C_{1-4}$ alkyl group, $$(C_xH_{2x}O)_mZ$$

where x, m and Z are as defined above, or oxygen provided only one $R_4$ is oxygen, $R_5$ is a $C_{1-22}$ alkyl, aryl or aryl alkyl group, X is halide, and Y is N, S or P.

The compounds of Formula V are formed in substantially the same manner as those of Formula II except that a mixture of $R_1OH$ and $$Z(OC_xH_{2x})_mOH$$

in the desired ratio is used in place of $R_1OH$ or, alternatively, the compounds of Formula II are heated with less than $3-a$ equivalents of $$Z(OC_xH_{2x})_mOH$$

under conditions such that $R_1OH$ is removed from the system.

Examples of illustrative compounds follow:

[H(OC$_2$H$_4$)$_5$O](CH$_3$)(C$_2$H$_5$O)SiCH$_2$N$^+$(CH$_3$)$_2$C$_{12}$H$_{25}$ Cl$^-$
[C$_{12}$H$_{25}$(OC$_2$H$_4$)$_3$O](CH$_3$O)$_2$Si(CH$_2$)$_3$N$^+$(C$_2$H$_5$)$_2$C$_6$H$_5$ Cl$^-$
[H(OC$_4$H$_8$)$_6$O](C$_2$H$_5$O)$_2$Si(CH$_2$)$_3$N$^+$[(C$_2$H$_4$O)$_{10}$H]$_2$C$_{18}$H$_{37}$ Br$^-$
[CH$_3$CO(OC$_2$H$_4$)$_3$O]$_2$(C$_2$H$_5$O)Si(CH$_2$)$_2$N$^+$[(C$_2$H$_4$O)C$_2$H$_5$](C$_6$H$_5$CH$_3$)$_2$ Cl$^-$
[H(OC$_2$H$_4$)$_{12}$O](C$_4$H$_8$O)$_2$SiCH$_2$N$^+$[(C$_2$H$_4$O)$_4$COCH$_3$]$_2$C$_{14}$H$_{29}$ Cl$^-$
[C$_{16}$H$_{33}$(OC$_2$H$_4$)$_3$O](C$_2$H$_5$)(CH$_3$O)SiCH$_2$N$^+$(O)$^-$(CH$_3$)C$_6$H$_{13}$
[H(OC$_3$H$_6$)$_{12}$O](C$_2$H$_5$O)$_2$SiCH$_2$N$^+$(C$_2$H$_5$COOH)(CH$_3$)C$_{10}$H$_{21}$ Cl$^-$
[C$_2$H$_5$(OC$_2$H$_4$)$_{14}$O]$_2$(C$_4$H$_9$O)Si(CH$_2$)$_3$N$^+$(C$_4$H$_8$OH)(CH$_3$)C$_{14}$H$_{29}$ Cl$^-$
[H(OC$_2$H$_4$)$_{16}$O]$_2$(CH$_3$O)SiCH$_2$P$^+$(CH$_3$)$_2$C$_6$H$_4$C$_2$H$_5$ Cl$^-$
[C$_3$H$_7$(OC$_2$H$_4$)$_6$O](C$_2$H$_5$)(CH$_3$O)SiCH$_2$P$^+$[(C$_2$H$_4$O)$_8$H]$_2$C$_8$H$_{17}$ Br$^-$
[CH$_3$CO(OC$_2$H$_4$)$_2$O]$_2$(CH$_3$O)Si(CH$_2$)$_2$P$^+$[(C$_3$H$_6$O)$_3$C$_2$H$_5$](C$_4$H$_9$)$_2$ Cl$^-$
[H(OC$_4$H$_8$)$_2$O](C$_{12}$H$_{25}$)(CH$_3$O)SiCH$_2$P$^+$(O)$^-$(CH$_3$)C$_6$H$_5$ $_2$
[C$_{14}$H$_{29}$(OC$_2$H$_4$)$_6$O](CH$_3$O)$_2$SiCH$_2$P$^+$(C$_3$H$_6$COOH)$_2$CH$_3$ Cl$^-$
[H(OC$_2$H$_4$)$_8$O]$_2$(C$_4$H$_9$O)SiCH$_2$P$^+$(C$_3$H$_6$OH)$_2$C$_2$H$_5$ Br$^-$
[H(OC$_2$H$_4$)$_{10}$O]$_2$(C$_3$H$_7$O)SiCH$_2$S$^+$(CH$_3$)C$_6$H$_{12}$C$_6$H$_5$ Cl$^-$
[H(OC$_4$H$_8$)$_2$O]$_2$(CH$_3$O)Si(CH$_2$)$_3$S$^+$[(C$_2$H$_4$O)$_4$H]CH$_3$ Br$^-$

[C₁₂H₂₅(OC₂H₄)₆O](CH₃)(CH₃O)SiCH₂S⁺[(C₃H₆O)₈CH₃]C₃H₇ Cl⁻

[CH₃CO(OC₂H₄)₃O](C₂H₅O)₂Si(CH₂)₂S⁺(C₂H₄OH)C₁₂H₂₅ Cl⁻

[CH₃(OC₃H₆)₁₂O](CH₃O)₂SiCH₂S⁺(C₃H₆COOH)CH₂C₆H₅ Br⁻

[H(C₂H₄O)₆O](C₁₂H₂₅)(CH₃O)SiCH₂S⁺(O)⁻C₁₄H₂₉

Commonly assigned copending patent application "Organosilane Compounds" by Heckert and Watt U.S. Ser. No. 570,539, filed Apr. 22, 1975 discloses the preparation of these compounds. (The disclosure of this application is herein incorporated by reference.)

$$[Z(OC_xH_{2x})_mO]_{3-a}-\underset{\underset{R_4}{\mid}}{\overset{\overset{(R_2)_a}{\mid}}{Si}}-CHR_3-\underset{\underset{R_4}{\mid}}{Y^+}-R_5\ X^- \qquad \text{VI.}$$

wherein Z is hydrogen, a $C_{1-18}$ alkyl group or a $C_{1-4}$ acyl group, $x$ is 2–4, $m$ is 1–20, $a$ is 0–2, $R_2$ is a $C_{1-18}$ alkyl group, $R_3$ is a $C_{1-18}$ alkyl group, $R_4$ is a $C_{1-12}$ alkyl, aryl or arylalkyl group, a carboxy-substituted $C_{1-4}$ alkyl group, $$(C_xH_{2x}O)_mZ$$

where $x$ is 2–4, $m$ is 1–20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide and Y is N, S or P.

The compounds of Formula VI are formed in the same manner as those of Formula III with the exception that $$Z(OC_xH_{2x})_mOH$$

is used in place of $$R_1OH$$

during the alcoholysis of the halo-silane. Alternatively, preparation may be effected by the heating of compounds of Formula III with $$Z(OC_xH_{2x})_mOH$$

under conditions such that all of the $$R_1OH$$

is removed from the system.

The following compounds illustrate the compounds of Formula VI.

[CH₃(OC₂H₄)₃O]₃SiCH(CH₃)N⁺(CH₃)₂C₁₈H₃₇ Cl⁻

[C₂H₅(OC₂H₄)O]₂CH₃SiCH(C₂H₅)N⁺(C₂H₄OH)₂C₁₄H₂₉ Cl⁻

[H(OC₄H₈)₈O]₃SiCH(C₄H₉)N⁺(C₂H₄COOH)(C₄H₉)CH₂C₆H₅ Cl⁻

[CH₃CO(OC₂H₄)₂O]₃SiCH(C₂H₅)N⁺(O)⁻(CH₃)C₁₀H₂₁

[H(OC₃H₆)₆O]₃SiCH(C₁₂H₂₅)N⁺[(C₂H₄O)₁₀H]₂CH₃ Br⁻

[C₁₂H₂₅(OC₂H₄)O]₃SiCH(C₃H₇)N⁺[(C₄H₈O)₃C₅H₁₀](C₂H₅)₂ Cl⁻

[C₁₀H₂₁(OC₂H₄)₄O]₃SiCH(C₂H₅)N⁺[(C₂H₄O)₆COCH₃]₂CH₃ Cl⁻

[H(OC₂H₄)₁₆O]₃SiCH(C₈H₁₇)P⁺(C₂H₅)₂C₆H₄C₄H₉ Cl⁻

[CH₃(OC₂H₄)₁₆O]₂C₁₂H₂₅SiCH(CH₃)P⁺(C₂H₄COOH)₂C₁₀H₂₁ Cl⁻

[C₂H₅OC(OC₂H₄)₅O]₃SiCH(CH₃)P⁺(C₂H₄OH)(CH₃)C₁₂H₂₅ Cl⁻

[H(OC₂H₄)₂O]₃SiCH(C₁₀H₂₅)P⁺(O)⁻(CH₃)C₁₆H₃₃

[H(OC₂H₄)₂O]₃SiCH(C₈H₁₇)P⁺[(C₂H₄O)₆H]₂C₄H₉ Br⁻

[CH₃(OC₄H₈)₂O]₃SiCH(CH₃)P⁺[(C₂H₄O)C₈H₁₇](CH₃)₂ Cl⁻

[C₁₀H₂₁(OC₂H₄)₂O]₃SiCH(C₆H₁₃)S⁺(CH₃)C₁₀H₂₁ Cl⁻

[H(OC₂H₄)₁₄O]₂CH₃SiCH(C₈H₁₇)S⁺(C₂H₄COOH)C₁₈H₃₇ Cl⁻

[H(OC₃H₆)₄O]₃SiCH(C₁₄H₂₉)S⁺(C₄H₈OH)C₆H₅ Cl⁻

[CH₃CO(OC₂H₄)₃O]₃SiCH(C₂H₅)S⁺(O)⁻C₁₈H₃₇

[C₁₂H₂₅(OC₂H₄)O]₃SiCH(C₃H₇)S⁺[(C₃H₆O)H]C₆H₁₃ Cl⁻

[H(OC₄H₈)₄O]₂CH₃SiCH(C₄H₉)S⁺[C₂H₄O)₈C₃H₇]CH₃ Br⁻

Commonly assigned copending patent application "Organosilane Compounds" by Heckert and Watt U.S. Ser. No. 570,537, filed Apr. 22, 1975 discloses the preparation of these compounds. (The disclosure of this application is herein incorporated by reference.)

$$[Z(OC_xH_{2x})_mO]_{3-(a+d)}-\underset{\underset{(OR_1)_d}{\mid}}{\overset{\overset{(R_2)_a}{\mid}}{Si}}-CHR_3-\underset{\underset{R_4}{\mid}}{\overset{\overset{R_4}{\mid}}{Y^+}}-R_5\ X^- \qquad \text{VII.}$$

wherein Z is hydrogen, a $C_{1-18}$ alkyl group or a $C_{1-4}$ acyl group, $x$ is 2–4, $m$ is 1–20, $R_2$ is a $C_{1-18}$ alkyl group, $R_1$ is a $C_{1-4}$ alkyl group, $a$ is 0 or 1, $d$ is 1 or 2 provided $a+d$ does not exceed 2, $R_3$ is a $C_{1-18}$ alkyl group, $R_4$ is a $C_{1-12}$ alkyl, aryl or arylalkyl group, a carboxy-substituted $C_{1-4}$ alkyl group, $(C_xH_{2x}O)_mZ$ where $x$, $m$ and Z are as defined above, or oxygen provided only one $R_4$ is oxygen, $R_5$ is a $C_{1-22}$ alkyl, aryl or arylalkyl group, X is halide and Y is N, S or P.

Compounds having Formula VII are prepared in substantially the same manner as those of Formula III except that a mixture of $$R_1OH$$

and $$Z(OC_xH_{2x})_mOH$$

in the desired ratio is used in place of $R_1OH$. Alternatively, the compounds of Formula III are heated together with less than $3-a$ equivalents of $$Z(OC_xH_{2x})_mOH$$

under conditions such that $R_1OH$ is removed from the system.

The following compounds are illustrative of the compounds of Formula VII:

[H(OC₂H₆)₆O](C₂H₅O)₂SiCHC₁₂H₂₅N⁺[(C₂H₄O)₁₀H]₂C₁₈H₃₇ Br⁻

[CH₃CO(OC₂H₄)₃O]₂(C₂H₅O)SiCHCH₃N⁺[(C₂H₄O)C₂H₅]₂C₆H₅CH₃ Cl⁻
[H(OC₂H₄)₁₂O](C₄H₈O)₂SiCHC₂H₅N⁺[(C₂H₄O)₄COCH₃]₂C₁₄H₂₉ Cl⁻
[C₁₆H₃₃(OC₂H₄)₃O](C₂H₅)(CH₃O)SiCHCH₃N⁺(O)⁻(CH₃)C₆H₁₃
[C₂H₅(OC₂H₄)₁₄O]₂(C₄H₉O)SiCHC₆H₁₃N⁺(C₆H₁₂OH)(CH₃)C₁₄H₂₉ Cl⁻
[H(OC₂H₄)₁₆O]₂(CH₃O)SiCHC₄H₉P⁺(CH₃)₂C₁₈H₃₇ Cl⁻
[CH₃CO(OC₂H₄)₂O]₂(CH₃O)SiCHC₁₆H₃₃P⁺[(C₃H₇O)₃C₂H₅](C₄H₉)₂ Cl⁻
[C₁₄H₂₉(OC₂H₄)₆O](CH₃O)₂SiCHCH₃P⁺(C₃H₆COOH)₂CH₃ Cl⁻
[H(OC₂H₄)₁₀O]₂(C₃H₇O)SiCHC₅H₁₁S⁺(CH₃)C₁₂H₂₅ Cl⁻
[H(OC₄H₈)₂O]₂(CH₃O)SiCHC₈H₁₇S⁺CH₃C₆H₅ Br⁻

Commonly assigned copending patent application "Organosilane Compounds" by Heckert and Watt U.S. Ser. No. 570,537, filed Apr. 22, 1975 discloses the preparation of the compounds. (The disclosure of this application is herein incorported by reference.)

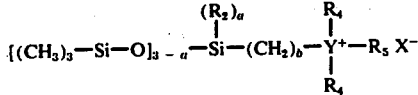

VIII.

wherein $a$ is 0–2, $R_2$ is $C_{1-18}$ alkyl group, $b$ is 1–3, $R_4$ is a $C_{1-12}$ alkyl, aryl or arylalkyl group, a carboxy-substituted $C_{1-14}$ alkyl group,

where $x$ is 2–4, $m$ is 1–20, and $Z$ is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide, and Y is N, S or P.

When $a$ is 0, a tris(trimethylsiloxy) silane is used as the starting reactant. Commercially available trihalosilanes and trimethylsilanes are used to produce the starting reactant. Subseqent reaction steps and conditions as discussed in the preparation of compounds of Formula I are used to produce the desired compound of Formula VI.

When $a$ is 1 or 2, a corresponding compound of Formula II is reacted with trimethylchlorosilane at an elevated temperature, e.g., 50° C. to 200° C. to obtain the desired organosilane.

Examples of compounds of Formula VIII are:
[(CH₃)₃SiO]₃SiCH₂N⁺(CH₃)₂C₁₄H₂₉ Cl⁻
[(CH₃)₃SiO]₂CH₃Si(CH₂)₃N⁺(CH₂COOH)₂C₆H₅ Cl⁻
[(CH₃)₃SiO]₃SiCH₂N⁺(C₂H₄OH)(CH₃)(C₁₂H₂₅) Cl⁻
[(CH₃)₃SiO]₃Si(CH₂)₂N⁺(O)⁻(CH₃C₈H₁₇
[(CH₃)₃SiO]₃SiCH₂N⁺[(C₂H₄O)₁₄H]₂CH₃ Cl⁻
[(CH₃)₃SiO]₂CH₃SiCH₂N⁺[(C₃H₆O)CH₃](CH₃)₂ Br⁻
[(CH₃)₃SiO]₃SiCH₂N⁺[(C₂H₄O)₄COCH₃]₂CH₃ Cl⁻
[(CH₃)₃SiO]₃Si(CH₂)₂P⁺(CH₃)₂C₁₀H₂₁ Br⁻
[(CH₃)₃SiO]₃SiCH₂P⁺(C₂H₄COOH)(C₆H₁₃)₂ Cl⁻
[(CH₃)₃SiO]₂CH₃Si(CH₂)₂P⁺(C₄H₈OH)(CH₃)C₁₀H₂₁ Cl⁻
[(CH₃)₃SiO]₃SiCH₂P⁺(O)⁻(CH₃)C₆H₅
[(CH₃)₃SiO]₃Si(CH₂)₃P⁺[(C₂H₄O)₈H]₂C₆H₁₃ Cl⁻
[(CH₃)₃SiO]₃SiCH₂P⁺[(C₃H₆O)₂C₇H₁₅](C₄H₉)₂ Br⁻
[(CH₃)₃SiO]₃SiCH₂S⁺(CH₃)C₁₈H₃₇ Cl⁻
[(CH₃)₃SiO]₃Si(CH₂)₂S⁺(C₂H₄COOH)C₁₂H₂₅ Br⁻
[(CH₃)₃SiO]₃Si(CH₂)₃S⁺(C₃H₆OH)C₆H₄CH₃ Br⁻
[(CH₃)₃SiO]₃Si(CH₂)₂S⁺(O)⁻C₁₄H₂₉
[(CH₃)₃SiO]₃SiCH₂S⁺[(C₂H₄O)₂₀H]CH₃ Br⁻
[(CH₃)₃SiO]₃Si(CH₂)₃S⁺[(C₂H₄O)C₁₄H₂₉]C₂H₅ Cl⁻

Commonly assigned copending patent application "Organosilane Compounds" by Heckert and Watt U.S. Ser. No. 570,538 filed Apr. 22, 1975 discloses the preparation of the compounds when $R_4$ s a carboxy-substituted alkyl group or

(The disclosure of this application is herein incorporated by reference.) U.S. Pat. Nos. 2,955,127, 3,624,120 and 3,658,867 discloses the compounds when $R_4$ is alkyl, aryl, arylalkyl or oxygen.

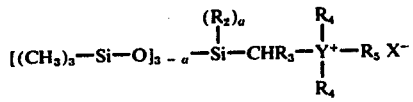

IX.

wherein $a$ is 0–2, $R_2$ is a $C_{1-18}$ alkyl group, $R_3$ is a $C_{1-18}$ alkyl group, $R_4$ is a $C_{1-12}$ alkyl, aryl or arylalkyl group, a carboxy-substituted $C_{1-4}$ alkyl group,

where $x$ is 2-4, $m$ is 1-20, and Z is hydrogen, a $C_{1-18}$ alkyl group or a $C_{1-14}$ acyl group, or oxygen provided only one $R_4$ is oxygen, $R_5$ is a $C_{1-22}$ alkyl, aryl or arylalkyl group, X is halide and Y is N, S or P.

When $a$ is 0, the compounds of Formula IX are prepared following the description given for the preparation of the compounds of Formula III with the exception that a tris(trimethylsiloxy)silane is used as the starting reactant. When $a$ is 1 or 2, a corresponding compound of Formula III is reacted with a trimethylchlorosilane at about 50° to 200° C. to produce the desired organosilane.

Illustrative compounds of Formula IX follow:
[(CH₃)₃SiO]₃SiCH(CH₃)N⁺(CH₃)₂C₁₈H₃₇ Cl⁻
[(CH₃)₃SiO]₂CH₃SiCH(C₂H₅)N⁻(C₂H₄OH)₂C₆H₄CH₃Cl⁻
[(CH₃)₃SiO]₃SiCH(C₄H₉)N⁺(C₃H₆COOH) (C₄H₉)₂ Cl⁻
[(CH₃)₃SiO]₃SiCH(C₂H₅)N⁺(O)⁻(CH₃)C₁₀H₂₁
[(CH₃)₃SiO]₃SiCH(C₁₂H₂₅)N⁺[(C₂H₄O)₁₀H]₂CH₃ Br⁻
[(CH₃)₃SiO]₃SiCH(C₃H₇)N⁺[(C₄H₈O)₃C₅H₁₀](C₂H₅)₂ Cl⁻
[(CH₃)₃SiO]₃SiCH(C₂H₅)N⁺[(C₂H₄O)₆COCH₃]₂CH₃ Cl⁻
[(CH₃)₃SiO]₃SiCH(C₈H₁₇)P⁺(C₂H₅)₂C₈H₁₇ Cl⁻
[(CH₃)₃SiO]₂C₂H₅SiCH(CH₃)P⁺(C₃H₆COOH)₂C₁₀H₂₁ Cl⁻
[(CH₃)₃SiO]₃SiCH(CH₃)P⁺(C₂H₄OH) (CH₃)C₁₂H₂₅ Cl⁻
[(CH₃)₃SiO)₃SiCH(C₁₀H₂₁)P⁺(O)⁻(CH₃)C₈H₁₇
[(CH₃)₃SiO]₃SiCH(C₈H₁₇)P⁺[(C₂H₄O)₆H]₂C₄H₉ Br⁻
[(CH₃)₃SiO]₃SiCH(CH₃)P⁺[(C₂H₄O)C₈H₁₇]₂C₆H₄C₂H₅ Cl⁻
[(CH₃)₃SiO]₃SiCH(C₆H₁₃)S⁺(CH₃)C₁₆H₃₃ Cl⁻
[(CH₃)₃SiO]₂CH₃SiCH(C₈H₁₇)S⁺(C₂H₄COOH)C₆H₅ Cl⁻
[(CH₃)₃SiO]₃SiCH(C₁₄H₂₉)S⁺(C₄H₈OH)CH₃ Cl⁻

[(CH₃)₃SiO]₃SiCH(C₂H₅)S⁺(O)⁻C₁₈H₃₇
[(CH₃)₃SiO]₃SiCH(C₃H₇)S⁺[(C₃H₆O)H]C₁₂H₂₅ Cl⁻
[(CH₃)₃SiO]₂C₁₈H₃₇SiCH(C₄H₉)S⁺[(C₂H₄O)₈C₃H₇]CH₃ Br⁻

Commonly assigned copending patent application "Organosilane Compounds" by Heckert and Watt U.S. Ser. No. 570,537, filed Apr. 22, 1975, discloses the preparation of these compounds. (The disclosure of this application is herein incorporated by reference.)

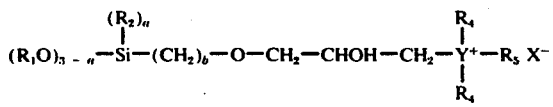
X.

wherein $R_1$ is a $C_{1-4}$ alkyl group, $a$ is 0–2, $R_2$ is a $C_{1-18}$ alkyl group, $b$ is 1–3, $R_4$ is a $C_{1-12}$ alkyl, aryl or arylalkyl group, a carboxy-substituted $C_{1-4}$ alkyl group, $(C_xH_{2x}O)_mZ$ where $x$ is 2–4, $m$ is 1–20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is halide, and Y is N, S or P.

The compounds of Formula X are prepared by initially reacting (when $a$ is 0 and $b$ is 3) trihalosilane with an alcohol ($R_1OH$) at 0° to 50° C. for 1 to 10 hours to produce a trialkoxysilane. This silane is then reacted with an allylglycidylether

in the presence of 0.01 to 0.1% chloroplatinic acid or platinum at 100° C. for 2 to 10 hours. The resultant product

is reacted with a tertiary amine, tertiary phosphine, or dialkysulfide in the presence of an acid in an inert solvent at 60° to 100° C. for 1 to 10 hours to produce the compound of Formula X.

When $a$ is 1 or 2, the preparation of the compounds is essentially the same except for the use of an alkyl substituted silane as the starting reactant.

When $b$ is 2 in formula X, a trihalovinylsilane of formula $X_3SiCH=CH_2$ (which is commercially available) is reacted with hydrogen bromide in the presence of peroxide or light to produce a beta-haloethyltrihalosilane. This compound is reacted with an alcohol, an allylglycidylether, and finally with an appropriate amine, phosphine, or sulfide in the manner discussed above for the preparation of the compounds of Formula X when $b$ is 3.

When $b$ is 1 in Formula X, the starting reactant is a commercially available trihalomethylsilane of formula $X_3SiCH_3$.

This silane is reacted with chlorine or, preferably a half mole of bromine and a half mole of chlorine in the presence of light (such as provided by an ordinary tungsten or fluorescent lamp). The resultant alpha-halomethyltrihalosilane is reacted with an alcohol, an allylglycidylether, and finally an appropriate amine, phosphine, or sulfide in the manner discussed above with the compounds of Formula X when b is 3.

The following compounds illustrate the compounds of Formula X.

(CH₃O)₃Si(CH₂)₃OCH₂CHOHCH₂N⁺(CH₃)₂C₁₆H₃₃ Cl⁻
(CH₃O)₂C₁₂H₂₅SiCH₂OCH₂CHOHCH₂N⁺(C₃H₆COOH)(C₄H₉)C₈H₁₇ Cl⁻
(C₂H₅O)₃Si(CH₂)₂OCH₂CHOHCH₂N⁺(C₂H₄OH)₂C₆H₅ Br⁻
(CH₃O)₃Si(CH₂)₃OCH₂CHOHCH₂N⁺(O)⁻(CH₃)C₈H₁₇
(CH₃O)₃SiCH₂OCH₂CHOHCH₂N⁺[(C₂H₄O)H]₂C₁₄H₂₉ Br⁻
(CH₃O)₂C₂H₅SiCH₂OCH₂CHOHCH₂N⁺[(C₃H₆O)₁₂C₂H₅](CH₃)₂ Cl⁻
(C₄H₉O)₃SiCH₂OCH₂CHOHCH₂N⁺[(C₂H₄O)₃COCH₃]₂CH₃ Br⁻
(CH₃O)₃SiCH₂OCH₂CHOHCH₂P⁺(C₄H₉)₂CH₂C₆H₅ Br⁻
(C₄H₉O)₃SiCH₂OCH₂CHOHCH₂P⁺(C₂H₄COOH)₂C₈H₁₇ Cl⁻
(CH₃O)₃Si(CH₂)₂OCH₂CHOHCH₂P⁺(C₂H₄OH)(C₂H₅)C₁₀H₂₁ Cl⁻
(CH₃O)₃SiCH₂OCH₂CHOHCH₂P⁺(O)⁻(CH₃)C₁₈H₃₇
(CH₃O)₃SiCH₂OCH₂CHOHCH₂P⁺[C₃H₆O)₁₈H]₂CH₃ Br⁻
(C₂H₅O)(CH₃)₂SiCH₂OCH₂CHOHCH₂P⁺[(C₂H₄O)CH₃]₂C₆H₁₃
(CH₃O)₃SiCH₂OCH₂CHOHCH₂S⁺(CH₃)C₆H₄CH₃ Cl⁻
(CH₃O)₂C₁₆H₃₇SiCH₂OCH₂CHOHCH₂S⁺(C₂H₄COOH)C₈H₁₇ Cl⁻
(CH₃O)₃Si(CH₂)₂OCH₂CHOHCH₂S⁺(C₂H₄OH)C₆H₁₃ Cl⁻
(C₂H₅O)₃SiCH₂OCH₂CHOHCH₂S⁺(O)⁻C₁₀H₂₁
(CH₃O)₃SiCH₂OCH₂CHOHCH₂S⁺[(C₂H₄O)₁₂H]CH₃ Br⁻
(C₂H₅O)₃SiCH₂OCH₂CHOHCH₂S⁻[(C₂h₄O)₂C₈H₁₇]C₂H₅ Br⁻

Commonly assigned copending patent application "Organosilane Compounds" by Heckert and Watt U.S. Ser. No. 570,531 filed Apr. 22, 1975 discloses the preparation of these compounds. (The disclosure of this application is herein incorporated by reference.)

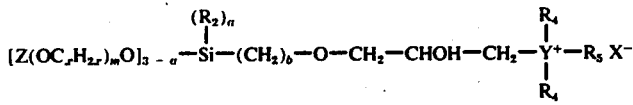

$$[Z(C_xH_{2x})_mO]_{3-a}-\underset{\underset{\displaystyle (R_2)_a}{|}}{Si}-(CH_2)_b-O-CH_2-CHOH-CH_2-\underset{\underset{\displaystyle R_4}{|}}{\overset{\overset{\displaystyle R_4}{|}}{Y^+}}-R_5 \ X^- \quad \text{XI.}$$

wherein Z is hydrogen, a $C_{1-8}$ alkyl group or a $C_{1-4}$ acyl group, x is 2–4, m is 1–20, a is 0–2, $R_2$ is a $C_{1-18}$ alkyl group, b is 1–3, $R_4$ is a $C_{1-12}$ alkyl, aryl, or arylalkyl group, a carboxy-substituted $C_{1-4}$ alkyl group, $$(C_xH_{2x}O)_mZ$$

where x is 2–4, m is 1–20, and Z is hydrogen, a $C_{1-18}$ alkyl group or a $C_{1-4}$ acyl group, or oxygen provided only one $R_4$ is oxygen, $R_5$ is a $C_{1-22}$ alkyl, aryl or arylalkyl group, X is a halide, and Y is N, S or P.

Compounds of Formula XI are prepared in a manner identical with that of Formula X except that $R_1OH$ is replaced by $$HO(C_xH_{2x}O)_mZ.$$

The following compounds are exemplary of Formula XI compounds.

[H(OC$_2$H$_4$)$_{20}$O]$_3$SiCH$_2$OCH$_2$CHOHCH$_2$N$^+$(CH$_3$)$_2$C$_{10}$H$_{21}$ Cl$^-$
[CH$_3$(OC$_3$H$_6$)$_{10}$O]$_2$CH$_3$SiCH$_2$OCH$_2$CHOHCH$_2$N$^+$(C$_2$H$_5$COOH)(C$_4$H$_9$)$_2$ Cl$^-$
[C$_2$H$_5$(OC$_2$H$_4$)$_2$O]$_3$Si(CH$_2$)$_3$OCH$_2$CHOHCH$_2$N$^+$(C$_2$H$_4$OH)$_2$(C$_8$H$_{17}$ Cl$^-$
[C$_8$H$_{17}$(OC$_2$H$_4$)O]$_3$SiCH$_2$OCH$_2$CHOHCH$_2$N$^+$(O)$^-$(C$_4$H$_9$)C$_6$H$_5$
[CH$_3$CO(OC$_2$H$_4$)$_6$O]$_3$Si(CH$_2$)$_2$OCH$_2$CHOHCH$_2$N$^+$[(C$_2$H$_4$O)$_{10}$H]$_2$CH$_3$ Cl$^-$
[H(OC$_3$H$_6$)$_8$O]$_2$C$_{16}$H$_{33}$SiCH$_2$OCH$_2$CHOHCH$_2$N$^+$[(C$_2$H$_4$O)$_8$C$_4$H$_9$](CH$_3$)$_2$ Br$^-$
[C$_2$H$_5$(OC$_2$H$_4$)$_4$O]$_3$SiCH$_2$OCH$_2$CHOHCH$_2$N$^+$[(C$_2$H$_4$O)$_2$COCH$_3$]$_2$CH$_3$ Br$^-$
[C$_{18}$H$_{39}$(OC$_2$H$_4$)$_3$O]$_3$SiCH$_2$OCH$_2$CHOHCH$_2$P$^+$(C$_2$H$_5$)$_2$C$_{14}$H$_{29}$ Cl$^-$
[H(OC$_3$H$_6$)$_8$]$_3$Si(CH$_2$)$_3$OCH$_2$CHOHCH$_2$P$^+$(C$_3$H$_6$COOH)$_2$C$_6$H$_{13}$ Cl$^-$
[C$_8$H$_{17}$(OC$_2$H$_4$)$_2$O]$_2$CH$_3$SiCH$_2$OCH$_2$CHOHCH$_2$P$^+$(C$_2$H$_4$OH)(CH$_3$)C$_8$H$_{17}$ Cl$^-$
[CH$_3$(OC$_3$H$_6$)O]$_3$si(CH$_2$)$_3$OCH$_2$CHOHCH$_2$P$^+$(O)$^-$(CH$_3$)C$_{10}$H$_{21}$
[C$_2$H$_5$(OH$_4$C$_2$)$_{12}$O]$_3$Si(CH$_2$)$_2$OCH$_2$CHOHCH$_2$P$^+$[(C$_2$H$_4$O)$_2$H]$_2$C$_6$H$_4$CH$_3$ Br$^-$
[CH$_3$CO(OC$_2$H$_4$)$_8$O]$_3$SiCH$_2$OCH$_2$CHOHCH$_2$P$^+$[(C$_3$H$_6$O)$_8$C$_2$H$_5$](C$_4$H$_9$)$_2$ Cl$^-$
[H(OC$_2$H)$_4$O]$_3$SiCH$_2$OCH$_2$CHOHCH$_2$S$^+$(CH$_3$)C$_{18}$H$_{37}$ Cl$^-$
[C$_{16}$H$_{33}$(OC$_2$H$_4$)$_6$O]$_2$C$_{12}$H$_{25}$SiCH$_2$OCH$_2$CHOHCH$_2$S$^+$(C$_3$H$_6$COOH)C$_{10}$H$_{21}$ Cl$^-$
[CH$_3$(OC$_4$H$_8$)$_4$O]$_3$SiCH$_2$OCH$_2$CHOHCH$_2$S$^+$(C$_4$H$_8$OH)C$_8$H$_{17}$ Br$^-$
[H(OC$_2$H$_4$)$_{14}$O]$_3$Si(CH)$_2$OCH$_2$CHOHCH$_2$S$^{+-}$(O)$^-$C$_{12}$H$_{14}$C$_6$H$_5$
[C$_9$H$_{19}$(OC$_2$H$_4$)O]$_3$SiCH$_2$OCH$_2$CHOHCH$_2$S$^+$[(C$_2$H$_4$O)$_6$H]C$_6$H$_{13}$ Cl$^-$
[C$_2$H$_5$CO(OC$_2$H$_4$)$_2$O]$_3$SiCH$_2$OCH$_2$CHOHCH$_2$S$^+$[(C$_4$H$_8$O)$_{12}$CH$_3$]C$_8$H$_{17}$ Cl$^-$

Commonly assigned copending patent application "Organosilane Compounds" by Heckert and Watt U.S. Ser. No. 570,531, filed Apr. 22, 1975 discloses the preparation of these compounds. (The disclosure of this application is herein incorporated by reference.)

$$[Z(C_xH_{2x})_mO]_{3-(m+d)}-\underset{\underset{\displaystyle (OR_1)_d}{|}}{\overset{\overset{\displaystyle (R_2)_a}{|}}{Si}}-(CH_2)_b-O-CH_2-CHOH-CH_2-\underset{\underset{\displaystyle R_4}{|}}{\overset{\overset{\displaystyle R_4}{|}}{Y^+}}-R_5 \ X^- \quad \text{XII.}$$

wherein Z is hydrogen, a $C_{1-18}$ alkyl group or a $C_{1-4}$ acyl group, x is 2–4, m is 1–20, $R_2$ is a $C_{1-18}$ alkyl group, $R_1$ is a $C_{1-4}$ alkyl group, a is 0 or 1, d is 1 or 2 provided a+d does not exceed 2, b is 1–3, $R_4$ is a $C_{1-12}$ alkyl, aryl or arylalkyl group, a carboxy-substituted $C_{1-4}$ alkyl group, $$(C_xH_{2x}O)_mZ$$

where x, m and Z are as defined above, or oxygen provided only one $R_4$ is oxygen, $R_5$ is a $C_{1-22}$ alkyl, aryl or arylalkyl group, X is halide, and Y is N, S or P.

These compounds are prepared in a manner similar to that described for the compounds of Example XI except that only a part of the $R_1OH$ is replaced by $$HO(C_xH_{2x}O)_mZ.$$

The following compounds are examples of compounds having the Formula XII.

[H(OC$_2$H$_4$)$_{12}$O](CH$_3$O)$_2$SiCH$_2$OCH$_2$CHOHCH$_2$N$^+$(CH$_3$)$_2$C$_{18}$H$_{37}$ Cl$^-$
[H(OC$_3$H$_6$O)$_3$O](C$_2$H$_5$O)(CH$_3$)Si(CH$_2$)$_2$OCH$_2$CHOHCH$_2$N$^+$(CH$_2$COOH)(CH$_4$H$_9$)$_2$ Cl$^-$
[C$_{12}$H$_{25}$(OC$_2$H$_4$)$_9$O](C$_2$H$_5$O)$_2$SiCH$_2$OCH$_2$CHOHCH$_2$N$^+$(C$_4$H$_8$OH)$_2$CH$_3$ Cl$^-$
[CH$_3$(OC$_4$H$_8$)$_2$O]$_2$(C$_4$H$_9$O)Si(CH$_2$)$_3$OCH$_2$CHOHCH$_2$N$^+$(O)$^-$(CH$_3$) C$_{16}$H$_{33}$
[CH$_3$CO(OC$_2$H$_4$)$_6$O]$_2$(CH$_3$O)SiCH$_2$OCH$_2$CHOHCH$_2$N$^+$[(C$_2$H$_4$O)$_8$H]$_2$CH$_3$ Br$^-$
[H(OC$_2$H$_4$)$_{18}$O](C$_2$H$_5$O)(C$_{16}$H$_{33}$)SiCH$_2$OCH$_2$CHOHCH$_2$N$^+$[(C$_2$H$_4$O)$_2$C$_{12}$H$_{25}$](CH$_3$)$_2$ Cl$^-$
[H(OC$_2$H$_4$)$_8$O](C$_2$H$_5$O)$_2$SiCH$_2$OCH$_2$CHOHCH$_2$P$^+$(CH$_3$)$_2$C$_6$H$_5$ Cl$^-$
[CH$_3$(OC$_2$H$_4$)$_6$O](C$_{12}$H$_{25}$)(CH$_3$O)SiCH$_2$OCH$_2$CHOHCH$_2$P$^+$[(C$_2$H$_4$O)$_6$OCH$_3$]$_2$(CH$_3$) Cl$^-$
[CH$_3$CO(OC$_3$H$_6$)$_4$O]$_2$(CH$_3$O)Si(CH$_2$)$_3$OCH$_2$CHOHCH$_2$P$^+$(C$_4$H$_8$OH)$_2$CH$_3$ Cl$^-$
[H(OC$_4$H$_8$)$_2$O](CH$_3$O)(CH$_3$)SiCH$_2$OCH$_2$CHOHCH$_2$S$^+$[(C$_2$H$_4$O)$_3$H]C$_2$H$_5$ Cl$^-$
[C$_{12}$H$_{25}$(OC$_2$H$_4$O)(C$_4$H$_9$O)$_2$Si(CH$_2$)$_2$OCH$_2$CHOHCH$_2$S$^+$(C$_3$H$_6$COOH)CH$_3$ Br$^-$
[C$_2$H$_5$CO(OC$_2$H$_4$)$_{10}$O]$_2$(C$_2$H$_5$O)SiCH$_2$OCH$_2$CHOHCH$_2$S$^+$(O)$^-$C$_{12}$H$_{25}$

Commonly assigned copending patent application "Organosilane Compounds" by Heckert and Watt U.S. Ser. No. 570,531, filed Apr. 22, 1975 discloses the preparation of these compounds. (The disclosure of this application is herein incorporated by reference.)

$$[(CH_3)_3-Si-O]_{3-a}-\overset{(R_2)_a}{\underset{}{Si}}-(CH_2)_b-O-CH_2-CHOH-CH_2-\overset{R_4}{\underset{R_4}{Y^+}}-R_5 \; X^- \qquad XIII.$$

wherein $a$ is 0–2, $R_2$ is a $C_{1-18}$ alkyl group, $b$ is 1–3, $R_4$ is a $C_{1-12}$ alkyl, aryl or arylalkyl group, a carboxy-substituted $C_{1-14}$ group, $$(C_xH_{2x}O)_mZ$$

where $x$ is 2–4, $m$ is 1–20, and Z is hydrogen, a $C_{1-18}$ alkyl group or a $C_{1}$-acyl group, or oxygen provided only one $R_4$ is oxygen, $R_5$ is a $C_{1-22}$ alkyl, aryl or arylalkyl group, X is halide, and Y is N, S or P.

Tris(trimethylsiloxy)silanes, which are prepared from commercially available trimethylhalosilanes and trihalosilanes, are used as the starting reactants when $a$ is 0. Subsequent reaction steps and conditions as discussed with the preparation of compounds of Formula X are used to produce the desired compound of Formula XIII.

When $a$ is 1 or 2, a compound of Formula X is reacted with trimethylchlorosilane at an elevated temperature, e.g. 50° to 200° C. to obtain the desired organosilane.

The following compounds are illustrative of the compounds of Formula XIII.

[(CH₃)₃SiO]₃SiCH₂OCH₂CHOHCH₂N⁺(CH₃)₂C₁₀H₂₁ Cl⁻

[(CH₃)₃SiO]₂CH₃SiCH₂OCH₂CHOHCH₂N⁺(C₂H₄COOH)(C₄H₉)₂ Cl⁻

[(CH₃)₃SiO]₃Si(CH₂)₃OCH₂CHOHCH₂N⁺(C₂H₄OH)₂C₈H₁₇ Cl⁻

[(CH₃)₃SiO]₃SiCH₂OCH₂CHOHCH₂N⁺(O)⁻(C₂H₅)C₆H₄C₂H₅

[(CH₃)₃SiO]₃Si(CH₂)₂OCH₂CHOHCH₂N⁺[(C₂H₄O)₁₀H]₂CH₃ Cl⁻

[(CH₃)₃SiO]₂C₂H₅SiCH₂OCH₂CHOHCH₂N⁺[(C₂H₄O)₆C₄H₉](CH₃)₂ Br⁻

[(CH₃)₃SiO]₃SiCH₂OCH₂CHOHCH₂N⁺[(C₃H₆O)₂COCH₃]₂CH₃ Br⁻

[(CH₃)₃SiO]₃SiCH₂OCH₂CHOHCH₂P⁺(C₂H₅)₂C₁₄H₂₉ Cl⁻

[(CH₃)₃SiO]₃Si(CH₂)₂OCH₂CHOHCH₂P⁺(C₃H₆COOH)₂C₆H₅ Cl⁻

[(CH₃)₃SiO]₂CH₃SiCH₂OCH₂CHOHCH₂P⁺(C₂H₄OH)(CH₃)C₈H₁₇ Cl⁻

[(CH₃)₃SiO]₃Si(CH₂)₃OCH₂CHOHCH₂P⁺(O)⁻(CH₃)C₁₀H₂₁

[(CH₃)₃SiO]₃Si(CH₂)₂OCH₂CHOHCH₂P⁺[(C₂H₄O)₂H]₂C₁₀H₂₁ Br⁻

[(CH₃)₃SiO]₃SiCH₂OCH₂CHOHCH₂P⁺[(C₃H₆O)₈C₂H₅](C₄H₉)₂ Cl⁻

[(CH₃)₃SiO]₃SiCH₂OCH₂CHOHCH₂S⁺(CH₃)C₁₈H₃₇ Cl⁻

[(CH₃)₃SiO]₂C₁₂H₂₅SiCH₂OCH₂CHOHCH₂S⁺(C₃H₆COOH)C₁₀H₂₁ Cl⁻

[(CH₃)₃SiO]₃SiCH₂OCH₂CHOHCH₂S⁺(C₄H₈OH)C₈H₁₇ Br⁻

[(CH₃)₃SiO]₃Si(CH₂)₂OCH₂CHOHCH₂S⁺(O)⁻C₁₆H₃₃

[(CH₃)₃SiO]₃SiCH₂OCH₂CHOHCH₂S⁺[(C₂H₄O)₆H]C₆H₄CH₃ Cl⁻

[(CH₃)₃SiO]₃SiCH₂OCH₂CHOHCH₂S⁺[(C₄H₈O)₁₂CH₃]C₈H₁₇ Cl⁻

U.S. Pat. No. 3,389,160 discloses compounds of Formula XIII when $R_4$ is an alkyl, aryl, or arylalkyl group. Commonly assigned patent application, "Organosilane Compounds" by Heckert and Watt, U.S. Ser. No. 570,538, filed Apr. 22, 1975 discloses the preparation of the other compounds. (The disclosure of this application is herein incorporated by reference.)

Siloxane oligomers of the above organosilanes are also useful in the present invention. Such oligomers are formed from the monomers by the controlled addition of from 1 to 100 equivalents of water, preferably in an inert solvent such as alcohol, tetrahydrofuran, etc. As used herein, "oligomers" is used to mean a degree of polymerization of from 2 to 100, preferably 2 to 20. A higher degree of polymerization adversely affects the ability of the compound to bond itself to the hard surface and is for this reason avoided. Examples of siloxane oligomers having varying degrees of polymerization are readily visualized from the above examples of organosilane monomers.

The water-soluble or water-dispersible nonionic material of this invention is normally solid, i.e. melts or liquefies between the temperature of 35° to 95° C., preferably from 40° to 65° C. and is preferably non-hygroscopic. A wide variety of nonionic materials fitting the above criteria are useful in the context of the present invention. Specific examples of materials suitable for use in this invention are:

(1) The condensation products of one mole of a saturated or unsaturated, straight or branched chain carboxylic acid having from about 10 to about 18 carbon atoms with from about 20 to about 50 moles of ethylene oxide, which liquefy between the temperatures of about 35° C. and about 95° C. and are solid at temperatures below about 35° C. The acid moiety can consist of mixtures of acids in the above-delineated carbon atoms range or it can consist of an acid having a specific number of carbon atoms within this range. The condensation product of one mole of coconut fatty acid having the approximate carbon chain length distribution of 2% $C_{10}$, 66% $C_{12}$, 23% $C_{14}$, and 9% $C_{16}$ with 35 moles of ethylene oxide is a specific example of a nonionic containing a mixture of different chain length fatty acid moieties. Other specific examples of nonionics of this type are: the condensation products of one mole of palmitic acid with 40 moles of ethylene oxide; the condensation product of one mole of myristic acid with 35 moles of ethylene oxide; the condensation product of one mole of oleic acid with 45 moles of ethylene oxide; and the condensation product of one mole of stearic acid with 30 moles of ethylene oxide.

(2) The condensation products of one mole of a saturated or unsaturated straight or branched chain alcohol having from about 10 to about 24 carbon atoms with from about 10 to about 50 moles of ethylene oxide which liquefy between the temperatures of about 35° C. and 95° C. and are solid at temperatures below about 35° C. The alcohol moiety can consist of alcohols in the above-delineated carbon atom range or it can consist of an alochol having a specific number of carbon atoms within this range. The condensation product of one mole of coconut alcohol having the approximate chain length distribution of 2% $C_{10}$, 66% $C_{12}$, 23% $C_{14}$, and 9% $C_{16}$ with 45 moles of ethylene oxide ($CNAE_{45}$) is a specific and highly preferred example of a nonionic containing a mixture of different chain length alcohol moieties. Other specific examples of nonionics of this type are the condensation products of one mole of tallow alcohol with 20 moles of ethylene oxide; the condensation products of one mole of lauryl alcohol with 35 moles of ethylene oxide; the condensation products of one mole of myristyl alcohol with 30 moles of ethylene oxide; and the condensation products of one mole of oleyl alcohol with 40 moles of ethylene oxide.

(3) Two specific examples of nonionic surface active agents suitable for use in this invention and not specifically classified herein are polyoxyethylene glyceride esters having a hydrophilic-lipophile balance (HLB) of 18.1 and polyoxyethylene lanolin derivatives having an HLB of 17.0. Both nonionics are manufactured by Atlas Chemical Industries, Inc.; the trade name of the former is G-1300 and the trade name of the latter is G-1795. The HLB number is an indication of the percentage weight of the hydrophilic portion of the nonionic molecule divided by 5.

(4) Amides which have a melting point between about 35° and 95° C. are also suitable for use in this invention. Specific examples are propyl amide, N-methyl amides having an acyl chain length of from about 10 to about 15 carbon atoms, pentyl anilide and anilides having a carbon chain length of from about 7 to about 12 carbon atoms, oleamide, amides of ricinoleic acid, N-isobutyl amides of pelargonic acid, capric acid, undecanoic acid and lauric acid, N-(2-hydroxyethyl) amides having a carbon chain length of from about 6 to about 10 carbon atoms, N-cyclopentyllauramide and N-cyclopentylstearamide.

(5) The polyethylene glycols having a molecular weight of from about 1400 to about 30,000, preferably from 4000 to 20,000. For example, Dow Chemical Company manufactures these nonionics in molecular weights of 20,000, 9500, 7500, 3400 and 1450. All of these nonionics are waxlike, solids which melt between 35° and 95° C.

(6) The condensation products of one mole of alkyl phenol wherein the alkyl chain contains from about 8 to about 18 carbon atoms with from about 25 to about 50 moles of ethylene oxide. Specific examples of these nonionics are the condensation products of one mole of decyl phenol with 40 moles of ethylene oxide; the condensation products of one mole of dodecyl phenol with 35 moles of ethylene oxide; the condensation products of one mole of tetradecyl phenol with 35 moles of ethylene oxide; the condensation products of one mole of hexadecyl phenol with 30 moles of ethylene oxide.

(7) Fatty acid containing from about 12 to about 30 carbon atoms which melt between 35° and 95° C. Specific examples of these nonionics are lauric acid, myristic acid, palmitic acid, stearic acid, tallow acid or mixtures of tallow acid and coconut acid, arachidic acid, behenic acid and ligoceric acid. Fatty acids are nonionic when utilized as a conglutinating agent. When the finished granules are utilized in alkaline solutions, however, the fatty acids are saponified to soap, an anionic surface active agent. Fatty acids having from 12 to 18 carbon atoms are preferred for use herein.

(8) Fatty alcohols containing from about 16 to about 30 carbon atoms which melt between 35° and 95° C. Specific examples of these nonionics are 1-hexadecanol, 1-octadecanol, 1-eicosanol, 1-heneicosanol, 3-docosanol, 1-tetracosanol and 1-octacosanol.

Normally solid water-soluble or -dispersible materials other than those listed above are also used in this invention provided they are compatible with the organosilane.

According to one aspect of this invention, the organosilane and nonionic material are made into a slurry by heating the normally solid nonionic material to a temperature sufficient to melt it and thereafter mixing with it the organosilane material. The slurry contains the organosilane and the nonionic material in a weight ratio of from 4:1 to 1:50, preferably 2:1 to 1:5.

Prills are made from the above-described slurry by any convenient method. One method comprises spraying the slurry into a cooling tower. As the spray droplets fall through the cooling tower, they solidify and are collected at the base of the tower. In a typical spray cooling operation, the slurry is sprayed into the top of the tower, the height of which can vary considerably. At the base of the tower, a source of cool air, i.e. air having a temperature from 5° to 20° C. is introduced. The prill particle size is controlled by regulating the size of the spray drops of the slurry. In turn, the size of the spray drops will depend on factors such as the viscosity of the slurry, the spraying pressure and the nature of the spraying head, e.g. the outlet orifice size. Generally, the particle diameter of the prills of this invention is below about 1 mm. The above parameters are determined by routine experimentation. The resultant prills are spherical in form with the organosilane and nonionic material forming a homogenous mass.

Another method of forming prills involves the addition of the slurry of the organosilane and nonionic material to an agitated cooling bath containing liquid Freon. As the slurry contacts the Freon, prills are formed. Such prills are thereafter collected in any conventional manner.

Still another method of making prills involves the encapsulation of the organosilane by the normally solid nonionic material. Any one of the many known encapsulation techniques may be used.

Marumerizing techniques may also be used in producing prills containing the organosilane and nonionic material in the ratio as herein described.

Inert fillers such as sodium sulfate, sulfite, bicarbonate, acetate, and anhydrous citrate and sucrose or known prilling aids may be used in making the prills of this invention.

The prills of this invention are added to a wide variety of detergent compositions which contain moisture and have a pH above 7 and/or an electrolyte content. Detergent compositions intended for use on metallic or vitreous surfaces where a soil release benefit is desired utilize the hereindescribed prills. Such compositions contain water-soluble organic, nonionic, zwitterionic, ampholytic detergents or mixtures thereof. U.S. Pat. No. 3,579,454, issued May 18, 1971 to Everett J. Collier, Col. 11, line 49 to Col. 13, line 64, discloses detergents of the above class and is herein incorporated by reference. Such detergent compositions also contain water either in a free of hydrated form and contain an electrolyte and/or have an alkaline pH, i.e. a pH above 7.0.

If an anionic detergent is used, the organosilane preferably has a total of no more than 20 carbon atoms in the $R_2$, $R_3$, $R_4$ (when $R_4$ is an alkyl, aryl, arylalkyl group or a carboxy-substituted alkyl group) and $R_5$ groups. Additionally, $R_2$, $R_3$ and $R_5$ contain 1 to 12 carbon atoms and, when Z is an alkyl group, it contains 1 to 3 carbon atoms. Also $R_1$ is either the alkyl group or $$Z(OC_xH_{2x})_m.$$

The prills of this invention are added to a detergent composition at a level such that the ratio of organosilane exclusive of the nonionic prilling material) to detergent is from 1:1 to 1:10,000, preferably 1:1 to 1:500, most preferably 1:3 to 1:60.

A preferred detergent composition which contains the prills are automatic dishwasher detergent compositions. Such preferred compositions consist essentially of from 0.01% to 5%, preferably 0.1% to 2%, of the organosilane; from 0.1% to 15%, preferably 1% to 5% of a water-soluble nonionic organic detergent, from 5% to 60%, preferably 30% to 50% of a water-soluble organic or inorganic alkaline builder salt; and the balance inert filler salts. Suitable alkaline builder salts include sodium tripolyphosphate, sodium citrate, sodium carbonate, and sodium nitrilotriacetate. Suitable inert filler salts include sodium sulfate and chloride.

An alkali metal silicate having a $SiO:M_2O$ ratio of from 3.6:1 to 1:2 (where M = alkali metal, preferably sodium) at a level of from 7% to 35%, preferably 10% to 20% may optionally be added to the automatic dishwasher detergent composition. A chlorine bleach capable of giving the composition from 0.2% to 10%, preferably 0.5% to 5% available chlorine content is also optionally included. Chlorinated trisodium phosphate and sodium dichlorocyanurate are preferred chlorine bleaches. An alkali metal base, e.g. sodium or potassium hydroxide is added at a level of from 10% to 4 %, preferably 10% to 30% when the composition is used for commercial dishwashing machines.

The prills of this invention also find use in a detergent-free commercial automatic dishwashing machine composition. Such compositions consist essentially of from 0.01to 5%, preferably 0.1% to 2% of the organosilane, from 5% to 60%, preferably 30% to 50% of the alkaline builder salt, from 10% to 40%, preferably 10% to 30% of an alkali metal base, e.g. sodium and potassium hydroxide, and the balance inert filler salts. Suitable alkaline builder salts and filler salts are discussed above in connection with the automatic dishwashing machine detergent composition.

Prills of this invention also find use in a detergent-free toilet bowl cleaner. Such compositions consist essentially of from 0.01% to 5%, preferably 0.5% to 2% of the organosilane; from 50% to 90%, preferably 75% to 85% of sodium bisulfate; and the balance inert filler salts.

The above-stated amounts of organosilane in the composition is exclusive of the nonionic material which is associated with the organosilane as part of the prill. The organosilanes of this invention when not a part of a prill lose some of their efficacy upon storage when included in this composition. This is evident by the formation of water-insoluble excessively polymerized organosilanes. A significant improvement is realized when the organosilane forms a part of the hereindescribed prills.

EXAMPLE III

Prills produced by Marumerizing techniques have the following composition:

| | |
|---|---|
| Sodium sulfate | 62.5% |
| Coconut monoethanol amide | 6.5% |
| Dextrin | 4.5% |
| Polyvinylpyrolidone | 0.8% |
| Titanium dioxide | 2.7% |
|  $[(CH_3)_3SiO]_3-Si-CH_2-\overset{\underset{\displaystyle CH_3}{\mid}}{\underset{\underset{\displaystyle CH_3}{\mid}}{N^+}}-C_{12}H_{25}\ Cl^-$ | 23.0% |

EXAMPLE IV

An automatic dishwashing machine detergent composition is formulated as follows:

| | |
|---|---|
| Sodium tripolyphosphate | 44.0% |
| Chlorinated trisodiumphosphate | 9.1% |
| Tallow alcohol ethoxylated with 9 moles of ethylene oxide | 2.5% |
| Sodium silicate ($SiO_2 : Na_2O = 2.4$) | 13.0% |
| Water | 25.0% |
| Organosilane prill | 5.0% |
| Misc. (perfume, dyes, etc.) | balance |

The organosilane prill is the prill of Example I.

Continued washing with the above formulation shows improved cleaning with successive washes compared to continued washing with an identical formulation without the organosilane prill (wherein sodium sulfate is used in place of the prill).

Storage of the composition of this example under conditions of 25° and 40% relative humidity for a prolonged periods does not noticeably affect the ability of the composition to impart a soil release benefit to cooking utensils and tableware washed therewith. The same composition wherein the organosilane is not protected by means of the nonionic material has a lesser ability to impart soil release benefits to cooking utensils and tableware washed therewith when stored under the same conditions.

Substantially the same results are obtained when the prills of Examples II(a)–(j) are substituted for the prill of Example IV (keeping the organosilane content at the same level).

When the organosilane in the prill of Example I is replaced by an organosilane in the list immediately following and the resultant prill used in the automatic dishwashing machine detergent composition of Example IV, substantially the same soil release benefits are noticed even after prolonged periods of storage.

$C_2H_5O)_3SiCH_2N^+(CH_3)_2C_{12}H_{25}\ Cl^-$
$C_2H_5O)_3SiCH_2P^+(CH_3)_2C_{12}H_{25}\ Cl^-$
$(C_2H_5O)_3Si(CH_2)_2N^+(CH_3)_2C_{12}H_{25}\ Cl^-$
$(C_2H_5O)_3Si(CH_2)_3N^+(CH_3)_2C_{12}H_{25}\ Br^-$
$(C_2H_5O)_3SiCH_2N^+(CH_3)_2C_6H_{13}\ Cl^-$
$(CH_3O)_3SiCH_2N^+(CH_3)_2CH_2C_6H_5\ Cl^-$
$(C_2H_5O)_3SiCH_2N^+(CH_3)_2C_{18}H_{37}\ Cl^-$
$(C_2H_5O)_3SiCH_2S^+(CH_3)C_{18}H_{37}\ Cl^-$
$(C_4H_8O)_3SiCH_2N^+(CH_3)_2C_{12}H_{24}C_6H_5\ Cl^-$

CH$_3$O)$_3$SiCH$_2$N$^+$[(C$_3$H$_6$O)$_3$C$_2$H$_5$]$_2$C$_8$H$_{17}$ Cl$^-$
(C$_2$H$_5$O)$_3$Si(CH$_2$)$_3$N$^+$(C$_2$H$_5$)[(C$_4$H$_9$O)$_6$H]C$_4$H$_9$ Cl$^-$
(C$_2$H$_5$O)$_3$SiCH$_2$N$^+$(C$_3$H$_7$COOH)$_2$C$_8$H$_{17}$ Cl$^-$
(C$_2$H$_5$O)$_3$SiCH$_2$N$^+$[(C$_2$H$_4$O)$_4$COCH$_3$]$_2$C$_{18}$H$_{37}$ Cl$^-$
[(CH$_3$)$_3$SiO]$_3$SiCH$_2$N$^+$(CH$_3$)$_2$C$_{12}$H$_{25}$ Br$^-$
(C$_2$H$_5$O)$_3$SiCH(C$_{12}$H$_{25}$)N$^+$(C$_2$H$_5$)$_3$ Cl$^-$
(C$_2$H$_5$O)$_3$SiCH(C$_{12}$H$_{25}$)P$^+$(C$_2$H$_5$)$_3$ Cl$^-$
(CH$_3$O)$_2$CH$_3$SiCH(C$_{18}$H$_{37}$)N$^+$(CH$_3$)$_3$ Br$^-$
(CH$_3$O)$_2$CH$_3$SiCH(C$_{18}$H$_{37}$)S$^+$(CH$_3$)$_2$ Br$^-$
(C$_2$H$_5$O)$_3$SiCH$_2$N$^+$(O)$^-$(CH$_3$)C$_{14}$H$_{29}$
(C$_2$H$_5$O)$_3$SiCH$_2$S$^+$(O)$^-$C$_{14}$H$_{29}$
(CH$_3$O)$_3$Si(CH$_2$)$_3$N$^+$(CH$_3$)$_2$C$_6$H$_4$C$_3$H$_7$ Cl$^-$
(CH$_3$O)$_3$SiCH$_2$N$^+$(C$_2$H$_4$OH) (CH$_3$)C$_{12}$H$_{25}$ Cl$^-$
(CH$_3$O)$_3$Si(CH$_2$)$_3$OCH$_2$CHOHCH$_2$N$^+$(CH$_3$)$_2$C$_8$H$_{17}$ Cl$^-$
(C$_2$H$_5$O)$_2$C$_4$H$_9$SiCH$_2$N$^+$(CH$_3$)$_2$C$_{12}$H$_{25}$ Cl$^-$
[H(OC$_2$H$_4$)$_{18}$O]]$_3$SiCH$_2$N$^+$(C$_2$H$_5$)$_2$C$_{18}$H$_{37}$ Cl$^-$
[CH$_3$(OC$_2$H$_4$)$_{12}$O]$_2$CH$_3$SiCH$_2$N$^+$(CH$_3$)$_2$C$_{12}$H$_{25}$ Br$^-$
[CH$_3$CO(OC$_2$H$_4$)$_4$]$_3$Si(CH$_2$)$_3$N$^+$(CH$_3$)$_2$C$_{10}$H$_{21}$ Cl$^-$
[H(OC$_2$H$_4$)$_8$](CH$_3$O)$_2$SiCH$_2$N$^+$(CH$_3$)$_2$C$_{12}$H$_{25}$ Cl$^-$
[CH$_3$(OC$_2$H$_4$)$_6$O]$_3$SiCH(C$_{12}$H$_{25}$)N$^+$(CH$_3$)$_3$ Br$^-$
[H(OC$_2$H$_4$)$_2$O]$_2$(CH$_3$O)SiCH(C$_8$H$_{17}$)N$^+$(CH$_3$)$_2$C$_6$H$_{13}$ Cl$^-$
[(CH$_3$)$_3$SiO]$_3$SiCH(C$_{16}$H$_{33}$)N$^+$(CH$_3$)$_2$C$_4$H$_9$ Cl$^-$
[H(OC$_2$H$_4$)$_4$O]$_3$SiCH$_2$OCH$_2$CHOHCH$_2$N$^+$(CH$_3$)$_2$C$_{12}$H$_{25}$ Cl$^-$
[CH$_3$(OC$_2$H$_4$)$_8$O]$_2$(CH$_3$O)SiCH$_2$OCH$_2$CHOHCH$_2$N$^+$(C$_4$H$_9$)$_3$ Cl$^-$
[(CH$_3$)$_3$SiO]$_3$SiCH$_2$OCH$_2$CHOHCH$_2$N$^+$(CH$_3$)$_2$C$_{14}$H$_{29}$ Br$^-$
[(CH$_3$)$_3$SiO]$_3$SiCH$_2$OCH$_2$CHOHCH$_2$P$^+$(CH$_3$)$_2$C$_{14}$H$_{29}$ Br$^-$
Siloxane dimer of (C$_2$H$_5$O)$_3$SiCH$_2$N$^+$(CH$_3$)$_2$C$_{12}$H$_{25}$ Cl$^-$
Siloxane dimer of (C$_2$H$_5$O)$_2$(CH$_3$)SiCH$_2$N$^+$(CH$_3$)$_2$C$_{16}$H$_{33}$ Cl$^-$
Siloxane trimer of (CH$_3$O)$_3$Si(CH$_2$)$_3$P$^+$(CH$_3$)$_2$C$_{12}$H$_{25}$ Cl$^-$
Siloxane dimer of (CH$_3$O)$_3$SiCH$_2$S$^+$(CH$_3$)C$_{12}$H$_{25}$ Cl$^-$

What is claimed is:

1. A prill containing an organosilane compound which consists essentially of:
   a. an organosilane having the formula

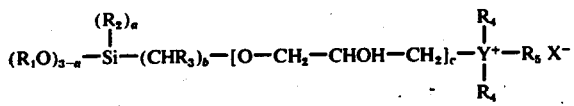

or is a siloxane oligmer thereof wherein R$_1$ is an alkyl group containing 1 to 4 carbon atoms, (CH$_3$)$_3$Si or Z (C$_x$H$_{2x}$)$_m$ where $x$ is 2 to 4, $m$ is 1 to 20, and Z is hydrogen, and alkyl group containing 1 to 18 carbons or an acyl group containing 1 to 4 carbon atoms; R$_2$ is an alkyl group contaning 1 to 18 carbon atoms; $a$ is 0 to 2; R$_3$ is hydrogen or an alkyl group containing 1 to 18 carbon atoms; $b$ is 1 to 3; $c$ is 0 or 1; R$_4$ is an alkyl, aryl or arylalkyl group containing 1 to 12 carbon atoms, a carboxy-substituted alkyl group containing 1 to 4 carbon atoms, (C$_x$H$_{2x}$O)$_m$Z where $x$, $m$ and Z are as defined above, or oxygen provided only one R$_4$ is oxygen and further provided that there is no X$^-$ when R$_4$ is oxygen; R$_5$ is an alkyl, aryl or arylalkyl group containing 1 to 22 carbon atoms; X is bromide or chloride; and Y is nitrogen, sulfur or phosphorus; and b. a water-soluble or water-dispersible, normally solid nonionic material which melts or liquifies between the temperatures of 35° and 95° C and is compatible with said organosilane compound in a weight ratio of organosilane to nonionic material of from 4:1 to 1:50.

2. The prill of claim 1 wherein the organosilane has the formula:

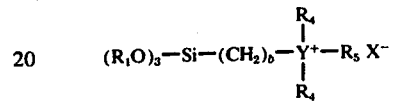

or is a siloxane oligomer thereof wherein R$_1$ is an alkyl group containing 1 to 4 carbon atoms; $b$ is 1 to 3; R$_4$ is a alkyl, aryl or arylalkyl group containing 1 to 12 carbon atoms, a carboxy-substituted alkyl group containing 1 to 4 carbon atoms, (C$_x$H$_{2x}$O)$_m$Z where $x$ is 2 to 4, $m$ is 1 to 20, and Z is hydrogen, an alkyl group containing 1 to 18 carbon atoms or an acyl group containing 1 to 4 carbon atoms, or oxygen provided only one R$_4$ is oxygen and further provided that when R$_4$ is oxygen there is no X$^-$; R$_5$ is an alkyl, aryl or arylalkyl group containing 4 to 22 carbon atoms; X is bromide or chloride; and Y is nitrogen, sulfur or phosphorus.

3. The prill of claim 1 wherein the organosilane has the formula

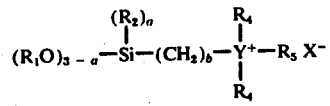

or is a siloxane oligomer thereof wherein R$_1$ is an alkyl group containing 1 to 4 carbon atoms; R$_2$ is an alkyl group containing 1 to 18 carbon atoms; $a$ is 1 or 2; $b$ is 1 to 3; R$_4$ is an alkyl, aryl or arylalkyl group containing 1 to 12 carbon atoms, a carboxy-substituted alkyl group containing 1 to 4 carbon atoms, (C$_x$H$_{2x}$O)$_m$Z where $x$ is 2 to 4, $m$ is 1 to 20, and Z is hydrogen, an alkyl group containing 1 to 18 carbon atoms or an acyl group containing 1 to 4 carbon atoms, or oxygen provided only one R$_4$ is oxygen and further provided that when R$_4$ is oxygen there is no X$^-$; R$_5$ is an alkyl, aryl or arylalkyl group containing 1 to 22 carbon atoms; X is bromide or chloride; and Y is nitrogen, sulfur or phosphorus.

4. The prill of claim 1 wherein the organosilane has the formula

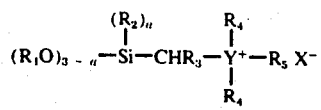

or is a siloxane oligomer thereof wherein $R_1$ is an alkyl group containing 1 to 4 carbon atoms; $R_2$ is an alkyl group containing 1 to 18 carbon atoms; $a$ is 0 to 2; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms

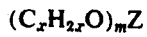

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided than when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

5. The prill of claim 1 wherein the organosilane has the formula

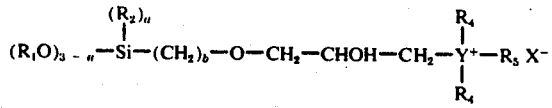

or is a siloxane oligomer thereof wherein $R_1$ is an alkyl group containing 1 to 4 carbon atoms; $R_2$ is an alkyl group containing 1 to 18 carbon atoms; $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms,

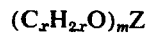

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

6. The prill of claim 1 wherein $b$ is 1.

7. The prill of claim 1 wherein the organosilane and nonionic material form a substantially homogeneous mass.

8. The prill of claim 1 wherein the organosilane is encapsulated by the nonionic material.

9. The prill of claim 1 wherein the ratio of organosilane to nonionic material is from 2:1 to 1:5.

10. The prill of claim 1 wherein the nonionic material is a polyethyleneglycol having a molecular weight of from 4000 to 20,000.

11. The prill of claim 1 wherein said normally solid nonionic material melts or liquifies between the temperature of 35° and 95° C and is selected from the group consisting of (1) the condensation products of 1 mole of a saturated or unsaturated, straight or branched chain carboxylic acid having from about 10 to about 18 carbon atoms with from about 20 to about 50 moles of ethylene oxide; (2) the condensation products of 1 mole of saturated or unsaturated, straight or branched chain alcohol having from about 10 to about 24 carbon atoms with from about 10 to about 50 moles of ethylene oxide; (3) polyoxyethylene glyceride esters having a hydrophilic-lyophile balance of 18.1; (4) polyoxyethylene lanolin derivatives having a hydrophilic-lyophile balance of 17.0; (5) amides; (6) polyethylene glycols having a molecular weight of from about 1,400 to about 30,000; (7) the condensation products of 1 mole of alkylphenol wherein the alkyl chain contains from about 8 to about 18 carbon atoms with from about 25 to about 50 moles of ethylene oxide; (8) fatty acid containing from about 12 to about 30 carbon atoms; (9) fatty alcohols containing from about 16 to about 30 carbon atoms; (10) water-soluble wax; (11) and mixtures thereof.

12. The prill of claim 1 wherein said nonionic material is nonhydrogroscopic.

13. The prill of claim 1 wherein the organosilane has the formula

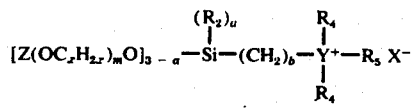

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms, $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms,

where $x$, $m$ and Z are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

14. The prill of claim 1 wherein the organosilane has the formula

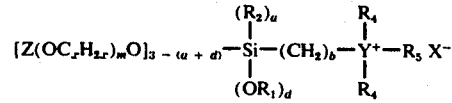

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $R_1$ is an alkyl group containing 1 to 4 carbon atoms, $a$ is 0 or 1; $d$ is 1 or 2 provided $a+d$ does not exceed 2; $b$ is 1 to 3; $R_4$ is an alkyl, aryl or arylalkyl group containing 1 to 12 carbon atoms, a carboxy-substituted alkyl group containing 1 to 4 carbon atoms,

where $x$, $m$ and Z are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

15. The prill of claim 1 wherein the organosilane has the formula

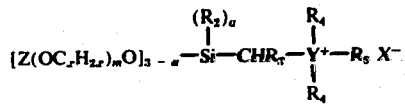

or is a siloxane digomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $a$ is 0 to 2; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms,

where $x$, $m$ and Z are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

16. The prill of claim 1 wherein the organosilane has the formula

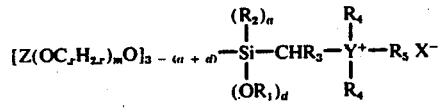

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $R_1$ is an alkyl group containing 1 to 4 carbon atoms; $a$ is 0 or 1, $d$ is 1 or 2 provided $2+d$ does not exceed 2; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms,

where $x$, $m$ and Z are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

17. The prill of claim 1 wherein the organosilane has the formula

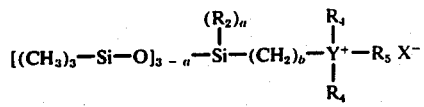

or is a siloxane oligomer thereof wherein $R_2$ is an alkyl group containing 1 to 18 carbon atoms; $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms,

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

18. The prill of claim 1 wherein the organosilane has the formula

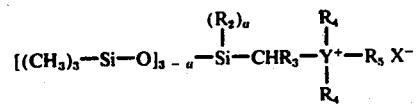

or is a siloxane oligomer thereof wherein $R_2$ is an alkyl group containing 1 to 18 carbon atoms; $a$ is 0 to 2; $R_3$ is an alkyl group containing 1 to 18 carbon atoms; $R_4$ is an alkyl, aryl or arylalkyl group containing 1 to 12 carbon atoms, a carboxy-substituted alkyl group containing 1 to 4 carbon atoms,

where $x$ is 2 to 4, $m$ is 1 to 20, and Z is hydrogen, an alkyl group containing 1 to 18 carbon atoms or an acyl group containing 1 to 4 carbon atoms, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

19. The prill of claim 1 wherein the organosilane has the formula

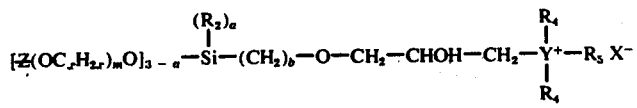

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $a$ is 0 to 2; $b$ is 1 to 3; $R_4$ is an alkyl, aryl or arylalkyl group containing 1 to 12 carbon atoms, a carboxy-substituted alkyl group containing 1 to 4 carbon atoms, $(C_xH_{2x}O)_mZ$ where $x$, $m$ and $Z$ are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

20. The prill of claim 1 wherein the organosilane has the formula

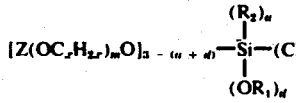—Si—(CH$_2$)$_b$—O—CH$_2$—CHOH—CH$_2$—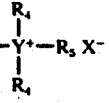

or is a siloxane oligomer thereof wherein Z is hydrogen, an alkyl group containing 1 to 18 carbon atoms or an acyl group containing 1 to 4 carbon atoms, $x$ is 2 to 4, and $m$ is 1 to 20; $R_2$ is an alkyl group containing 1 to 18 carbon atoms; $R_1$ is an alkyl group containing 1 to 4 carbon atoms; $a$ is 0 or 1; $d$ is 1 or 2 provided $a+d$ does not exceed 2; $b$ is 1 to 3; $R_4$ is an alkyl, aryl or arylalkyl group containing 1 to 12 carbon atoms, a carboxy-substituted alkyl group containing 1 to 4 carbon atoms, $(C_xH_{2x}O)_mZ$ where $x$, $m$ and $Z$ are as defined above, or oxygen provided only one $R_4$ is oxygen and further provided that when $R_4$ is oxygen there is no $X^-$; $R_5$ is an alkyl, aryl or arylalkyl group containing 1 to 22 carbon atoms; X is bromide or chloride; and Y is nitrogen, sulfur or phosphorus.

* * * * *

UNITED STATES PATENT OFFICE
CERTIFICATE OF CORRECTION

PATENT NO. : 4,013,574
DATED : Mar. 22, 1977
INVENTOR(S) : John W. Leikhim et al.

It is certified that error appears in the above-identified patent and that said Letters Patent are hereby corrected as shown below:

Column 4, line 65, "amines phosphine" should be -- amine, phosphine --.

Column 6, line 25, "essentialy" should be -- essentially --.

Column 6, line 50, "$(C_2H_5O)(C_2H_5)_2Si(CH_2)_3S^+[(C_2H_4O)_5CH_3[C_8H_{17}$" should be -- $(C_2H_5O)(C_2H_5)_2Si(CH_2)_3S^+[(C_2H_4O)_5CH_3]C_8H_{17}$ --.

Column 9, line 36, "$[CH_3(OC_2H_4)_5O]_2CH_3SiCH_2)_3N^+(CH$" should be -- $[CH_3(OC_2H_4)_5O]_2CH_3Si(CH_2)_3N^+(CH$ --.

Column 9, line 43, "$[C_{16}H_{33}(OC_2H_4)_8O]_2C_6H_{13}SiCH_2N^+[(C_3H_6O)CH_3)_2$" should be -- $[C_{16}H_{33}(OC_2H_4)_8O]_2C_6H_{13}SiCH_2N^+[(C_3H_6O)CH_3](CH_3)_2$ --.

Column 9, line 50, "$[C_2H_5(OC_2H_4)O]_2CH_3Si(CH_2)_2P^-(C_4$" should be -- $[C_2H_5(OC_2H_4)O]_2CH_3Si(CH_2)_2P^+(C_4$ --.

Column 13, line 22, "incorpted" should be -- incorporated --.

Column 14, line 45, "$[(CH_3)_3SiO]_2CH_3SiCH(C_2H_5)N^-(C_2$" should be -- $[(CH_3)_3SiO]_2CH_3SiCH(C_2H_5)N^+(C_2$ --.

Column 16, line 62, "$(C_2H_5O)_3SiCH_2OCH_2CHOHCH_2S^-[(C_2h_4O$" should be -- $(C_2H_5O)_3SiCH_2OCH_2CHOHCH_2S^+[(C_2H_4O$ --.

Column 17, line 47, "$[C_2H_5(OC_2H_4)_4O]_3SiCH_2 \quad OCH_2CHOHCH_2N^+[(C_2$"

UNITED STATES PATENT OFFICE
CERTIFICATE OF CORRECTION

PATENT NO. : 4,013,574
DATED : Mar. 22, 1977
INVENTOR(S) : John W. Leikhim et al.

It is certified that error appears in the above-identified patent and that said Letters Patent are hereby corrected as shown below:

should be -- $[C_2H_5(OC_2H_4)_4O]_3SiCH_2OCH_2CHOHCH_2N^+[(C_2$ --.

Column 17, line 55, "$[CH_3(OC_3H_6)O]_3Si(CH_2)_3OCH_2CHOHCH_2P$" should be -- $[CH_3(OC_3H_6)O]_3Si(CH_2)_3OCH_2CHOHCH_2P$ --.

Column 19, line 21, "$C_1$-" should be -- $C_{1-4}$ --.

Column 22, line 63, "nonionic, zwitterionic" should be -- nonionic anionic, zwitterionic --.

Column 23, line 9, "when Z" should be -- when the Z --.

Column 23, line 18, "lane exclusion" should be -- lane (exclusion --.

Column 23, line 26, "of a water-soluble" should be -- of the water-soluble --.

Column 23, line 43, "4%" should be -- 40% --.

Column 24, after line 5, please insert the following --

When a detergent composition containing the prills of this invention is added to water, the nonionic material either solubilizes or disperses thereby freeing the organosilane. As previously discussed, the organosilane is able to bond to a metallic or vitreous surface and impart soil release properties thereto. It is theorized that the positively charged atom in the organosilane molecule is attracted to the negatively charged hard surface and is responsible for the organosilane deposition occurring from the dilute conditions in which the compositions of this invention are used.

UNITED STATES PATENT OFFICE
CERTIFICATE OF CORRECTION

PATENT NO. : 4,013,574
DATED : Mar. 22, 1977
INVENTOR(S) : John W. Leikhim et al.

It is certified that error appears in the above-identified patent and that said Letters Patent are hereby corrected as shown below:

The following examples are illustrative of this invention.

EXAMPLE I

A slurry is made containing 80% polyethylene glycol (PEG) having M.W. of 6000 and 20%

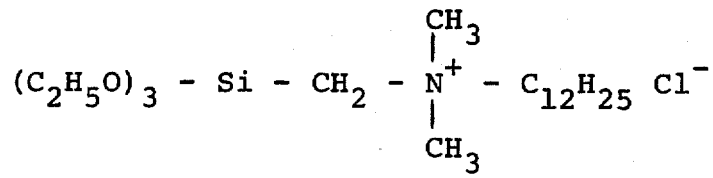

The PEG is heated to 80°C to melt it prior to adding the silane. The slurry is pumped to the top of a spray-cooling tower and atomized through a two-fluid nozzle under 30 p.s.i. pressure to form spray-droplets. A source of 5°C air is introduced into the bottom of the tower. As the spray-droplets fall, they are solidified by the air. Prills collected at the bottom of the tower are spherical in form and are about 0.45 mm to 0.70 mm in diameter. The prills are comprised of PEG and organosilane in a substantially homogeneous mass.

EXAMPLE II

Prills of the following compositions are prepared by the same process as described in Example I.

UNITED STATES PATENT OFFICE
CERTIFICATE OF CORRECTION

PATENT NO. : 4,013,574
DATED : Mar. 22, 1977
INVENTOR(S) : John W. Leikhim et al.

It is certified that error appears in the above-identified patent and that said Letters Patent are hereby corrected as shown below:

(a)

| | |
|---|---|
| PEG (M.W.=4000) | 50% |

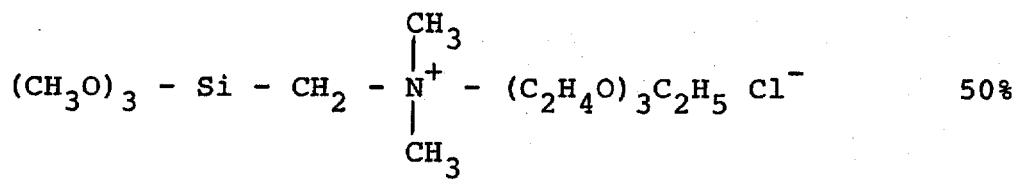

50%

(b)

| | |
|---|---|
| Palmitic acid ethoxylated with 40 moles of ethylene oxide | 80% |

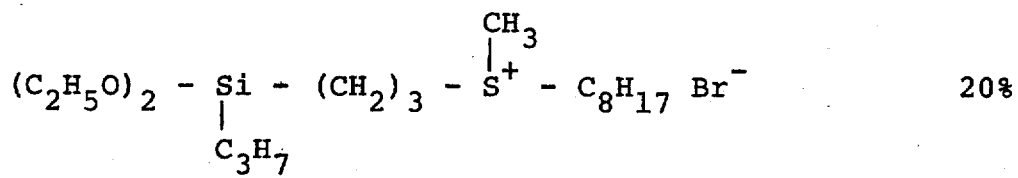

20%

(c)

| | |
|---|---|
| Coconut alcohol ethoxylated with 45 moles of ethylene oxide | 72% |

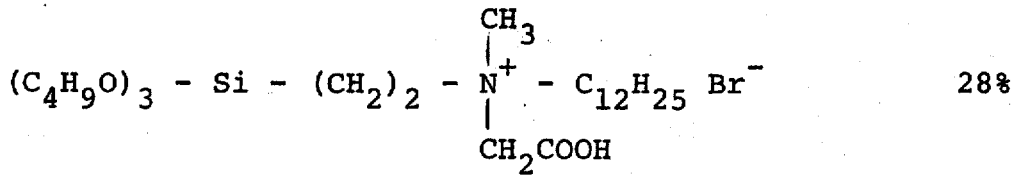

28%

UNITED STATES PATENT OFFICE
CERTIFICATE OF CORRECTION

PATENT NO. : 4,013,574
DATED : Mar. 22, 1977
INVENTOR(S) : John W. Leikhim et al.

It is certified that error appears in the above-identified patent and that said Letters Patent are hereby corrected as shown below:

(d)
Propyl amide                                                              68%

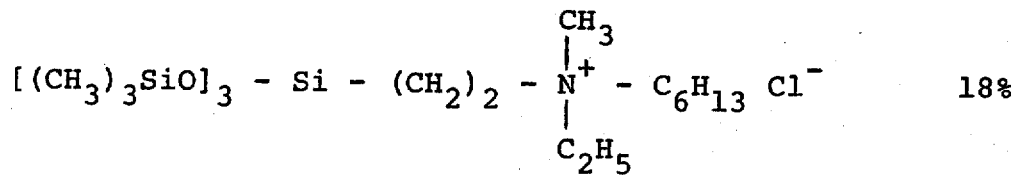
18%

Sodium Sulfate                                                            14%

(e)
Condensation product of dodecyl phenol
  with 35 moles ethylene oxide                                            95%

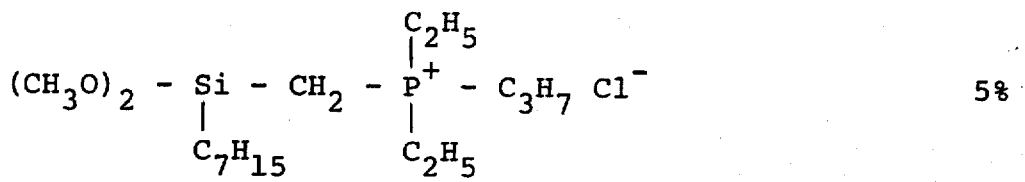
5%

(f)
Stearic Acid                                                              80%
Stearoyl alkanolamide                                                     15%

UNITED STATES PATENT OFFICE
CERTIFICATE OF CORRECTION

PATENT NO. : 4,013,574
DATED : Mar. 22, 1977
INVENTOR(S) : John W. Leikhim et al.

It is certified that error appears in the above-identified patent and that said Letters Patent are hereby corrected as shown below:

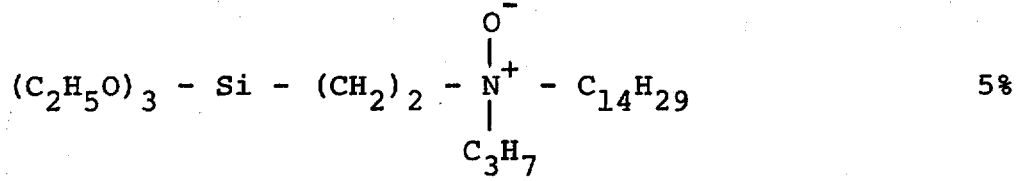  5%

(g)
1-Octadecanol  50%

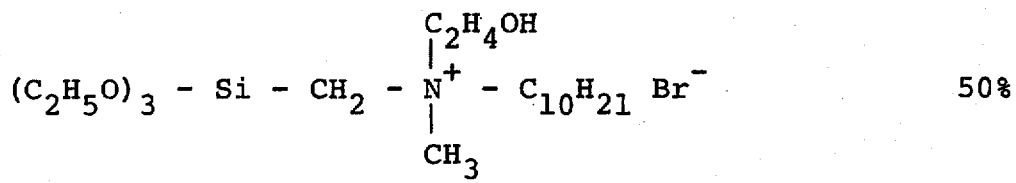  50%

(h)
Tallow Fatty Acid  75%

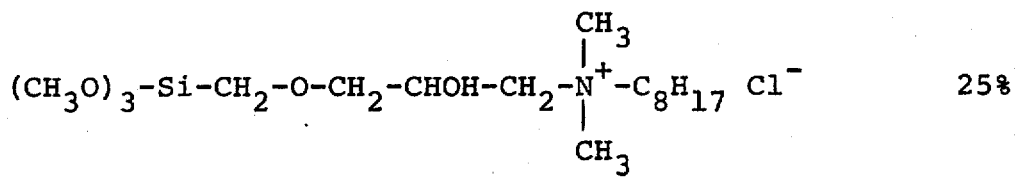  25%

(i)
Polyethylene glycol 9500  40%

UNITED STATES PATENT OFFICE
CERTIFICATE OF CORRECTION

PATENT NO. : 4,013,574
DATED : Mar. 22, 1977
INVENTOR(S) : John W. Leikhim et al.

It is certified that error appears in the above-identified patent and that said Letters Patent are hereby corrected as shown below:

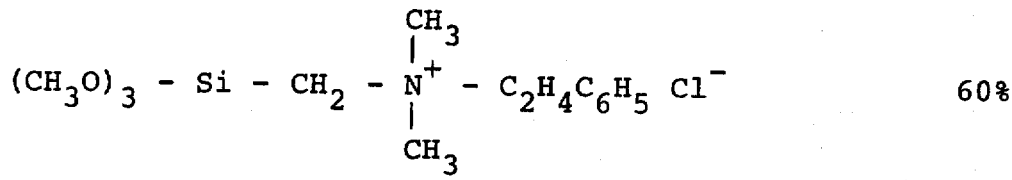  60%

(j)
Water-soluble wax  60%
Stearoyl ethanolamide  10%

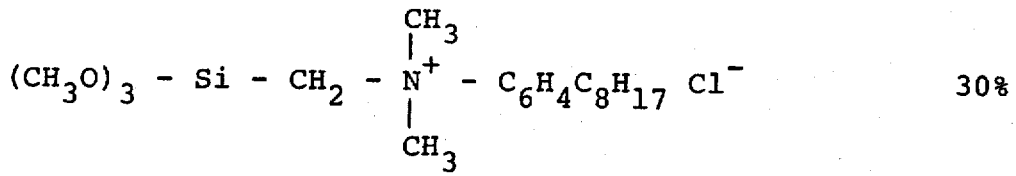  30%

Column 24, line 41, "25°" should be -- 25°C --.

Column 24, line 60, "$C_2H_5O)_3SiCH_2N^+(CH_3)_2C_{12}H_{25}Cl^-$" should be -- $(C_2H_5O)_3SiCH_2N^+(CH_3)_2C_{12}H_{25}Cl^-$ --.

Column 24, line 61, "$C_2H_5O)_3SiCH_2P^+(CH_3)_2C_{12}H_{25}Cl^-$" should be -- $(C_2H_5O)_3SiCH_2P^+(CH_3)_2C_{12}H_{25}Cl^-$ --.

Column 24, line 69, "$C_4H_8O)_3SiCH_2N^+(CH_3)_2C_{12}H_{24}C_6H_5Cl^-$" should be -- $(C_4H_8O)_3SiCH_2N^+(CH_3)_2C_{12}H_{24}C_6H_5Cl^-$ --.

UNITED STATES PATENT OFFICE
CERTIFICATE OF CORRECTION

PATENT NO. : 4,013,574
DATED : Mar. 22, 1977
INVENTOR(S) : John W. Leikhim et al.

It is certified that error appears in the above-identified patent and that said Letters Patent are hereby corrected as shown below:

Column 25, line 1, "$CH_3O)_3SiCH_2N^+[(C_3H_6O)_3C_2H_5]_2C_8H_{17}Cl^-$" should be -- $(CH_3O)_3SiCH_2N^+[(C_3H_6O)_3C_2H_5]_2C_8H_{17}Cl^-$ --.

Column 25, line 59, "hydrogen, and" should be -- hydrogen, an --.

Column 26, line 26, "a alkyl" should be -- an alkyl --.

Column 29, line 45, "2+d" should be -- a+d --.

Signed and Sealed this second Day of August 1977

[SEAL]

Attest:

RUTH C. MASON
Attesting Officer

C. MARSHALL DANN
Commissioner of Patents and Trademarks